US010005796B2

(12) United States Patent
Briseno et al.

(10) Patent No.: US 10,005,796 B2
(45) Date of Patent: Jun. 26, 2018

(54) SUBSTITUTED ANGULAR BISTETRACENES AND SUBSTITUTED ANGULAR BISOLIGOACENES AND ELECTRONIC DEVICES MADE WITH SAME

(71) Applicant: University of Massachusetts, Boston, MA (US)

(72) Inventors: Alejandro L. Briseno, Amherst, MA (US); Lei Zhang, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days. days.

(21) Appl. No.: 15/307,968

(22) PCT Filed: May 1, 2015

(86) PCT No.: PCT/US2015/028919
§ 371 (c)(1),
(2) Date: Oct. 31, 2016

(87) PCT Pub. No.: WO2015/168638
PCT Pub. Date: Nov. 5, 2015

(65) Prior Publication Data
US 2017/0050991 A1    Feb. 23, 2017

Related U.S. Application Data

(60) Provisional application No. 61/987,334, filed on May 1, 2014.

(51) Int. Cl.
*C07F 7/04* (2006.01)
*C07F 7/08* (2006.01)

(52) U.S. Cl.
CPC .......... *C07F 7/0809* (2013.01); *C07F 7/0827* (2013.01)

(58) Field of Classification Search
CPC ........................................................ C07F 7/08
USPC ........................................................ 556/432
See application file for complete search history.

(56) References Cited

U.S. PATENT DOCUMENTS

| 7,842,942 | B2 | 11/2010 | Brown et al. |
| 8,513,445 | B2 | 8/2013 | Facchetti et al. |
| 2007/0102696 | A1 | 5/2007 | Brown et al. |
| 2012/0048377 | A1 | 3/2012 | Winzenberg et al. |
| 2012/0074394 | A1* | 3/2012 | Facchetti ................ C07C 43/20 257/40 |

FOREIGN PATENT DOCUMENTS

WO    2015/168638 A1    11/2015

OTHER PUBLICATIONS

International Preliminary Report on Patentability dated Nov. 1, 2016, Int'l Application No. PCT/US2015/028919, entitled: Substituted Angular Bistetracenes and Substituted Angular Bisoligoacenes and Electronic Devices Made With Same.
Cao, Y. et al., "Why Bistetracenes Are Much Less Reactive Than Pentacenes in Diels-Alder Reactions With Fullerenes," *J. Am. Chem. Soc.*, 136(30): 10743-10751 (2014).
International Search Report, Written Opinion, and Search History for Int'l Application No. PCT/US2015/028919, titled: Substituted Angular Bistetracenes and Substituted Angular Bisoligoacenes and Electronic Devices Made With Same, dated Jul. 31, 2015.
Muller, A. M., et al.,"Exciton Fission and Fusion in Bis(tetracene) Molecules with Different Covalent Linker Structures," *J. Am. Chem. Soc.*, 129: 14240-14250 (2007).
Purushothaman,B. et al.,"Synthesis and Stability of Soluble Hexancene," *Organic Letters*, 12(9): 2060-2063 (2010).
Xiao, J., et al., "Synthesis and Characterization of a Stable Nonatwistacene," *Angew. Chem. Int. Ed.*, 51: 6094-6098 (2012).
Zade, S. S. and Bendikov, M., et al.,"Heptacene and Beyond: The Longest Characterized Acenes," *Angew. Chem. Int. Ed.* 49: 4012-4015 (2010).
Zhang, L. et al.,"Bistetracene: An Air-Stable, High-Mobility Organic Semiconductor with Extended Conjugation," *J. Am. Chem. Soc.*, 136(26): 9248-9251 (2014).
Zhang, L., et al.,"Triisopropylsilylethynyl-functionalized dibenzo[def, mno]chrysene: a solution-processed small molecule for bulk heterojunction solar cells," *J. Mater. Chem.*, 22: 4266-4268 (2012).
Zhang, L., et al.,"Triisopropylsilylethynl-Functionalized Graphene-Like Fragment Semiconductors: Synthesis, Crystal Packing, and Density Functional Theory Calculations," *Chem. Eur. J.*, 19: 17907-17916 (2013).
Zhang, L., et al., "Unconventional, Chemically Stable, and Soluble Two-Dimensional Angular Polycyclic Aromatic Hydrocarbons: From Molecular Design to Device Applications," *Acc. Chem. Res.*, 48: 500-509 (2015).

* cited by examiner

*Primary Examiner* — Sudhakar Katakam
*Assistant Examiner* — Kofi Adzamli
(74) *Attorney, Agent, or Firm* — Hamilton, Brook, Smith & Reynolds, P.C.

(57) ABSTRACT

We report the synthesis and characterization of novel bistetracenes, an unconventional, linearly extended conjugated core with eight fused rings. Also described are bisoligoacenes. In general, the properties and stability of large polycyclic aromatic hydrocarbons (PAHs) strongly depend on the mode of ring annellation and the topology of their it-electron systems, which are usually associated with the resonance stabilization energy in large PAHs.

16 Claims, 14 Drawing Sheets

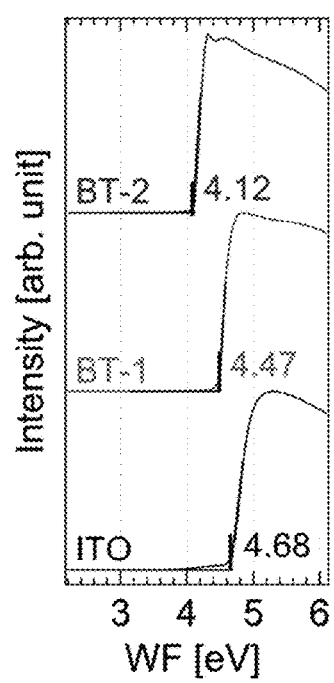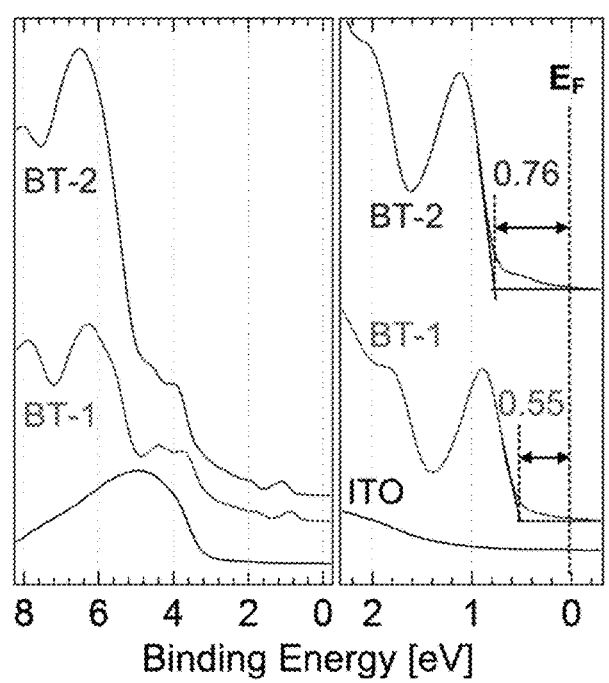
FIG. 7A    FIG. 7B    FIG. 7C

SUBSTITUTED ANGULAR BISTETRACENES AND SUBSTITUTED ANGULAR BISOLIGOACENES AND ELECTRONIC DEVICES MADE WITH SAME

RELATED APPLICATION

This application is the U.S. National Stage of International Application No. PCT/US2015/028919, filed on May 1, 2015, published in English, which claims the benefit of U.S. Provisional Application No. 61/987,334, filed on May 1, 2014. The entire teachings of the above applications are incorporated herein by reference.

GOVERNMENT SUPPORT

This invention was made with government support under the Office of Naval Research awards N000141110636 and N000141110211; and the Department of Energy Award No. DOE DE-SC0001087. The government has certain rights in the invention.

BACKGROUND OF THE INVENTION

Polyacenes with linearly annellated benzene units have received much attention in both experimental and theoretical studies because of their unique electronic structures.[1] In particular, they have been closely examined as semiconductor materials in organic field-effect transistors (OFETs) due to their relatively high charge-carrier mobility.[1b,1c] Since increased conjugation length could be beneficial for electronic coupling and reducing reorganization energies in the solid state, chemists have been pursuing acenes larger than pentacene, one of the most popular and well-studied materials for organic devices.[2] However, it is becoming clear that the higher acenes and peri-acenes suffer from reduced stability, due to the zig-zag peripheries, which lead to low resonance stabilization, small band gaps and high reactivity.[3] Although significant progress has been made in the development of higher acenes, only a handful have been successfully synthesized and characterized due to the multiple synthetic steps, poor solubility and extreme instability (sensitivity to light, oxygen, and polymerization).[4]

SUMMARY OF THE INVENTION

In general, the properties and stability of large polycyclic aromatic hydrocarbons (PAHs) strongly depend on the mode of ring annellation and the topology of their π-electron systems, which are usually associated with the resonance stabilization energy in large PAHs.[7] For example, the stability of polyacenes can be improved by changing the linearity of a condensed array to an angular analogue, such as V-shape and triangular geometries (FIG. 1).[8] The simple interpretation of the stability of these compounds can be obtained in the framework of the aromatic Clar sextet model, which states that a molecule with more benzenoid sextets increases the overall aromatic stabilization energy.[1d] These compounds have at least two sextets, which render them more stable, compared to linear analogs with only one sextet.[1d] Here, we report the synthesis of solution-processable, air stable, organic semiconductors with extended conjugation, namely, "bisoligotetracenes," and discuss their electronic/molecular structures, crystal packing, and performance in organic field-effect transistors. We also describe the synthesis of "bisoligoacenes."

Described herein are compounds, methods of making compounds, and field effect transistors that include the compounds.

One embodiment is a compound according to following structural formula:

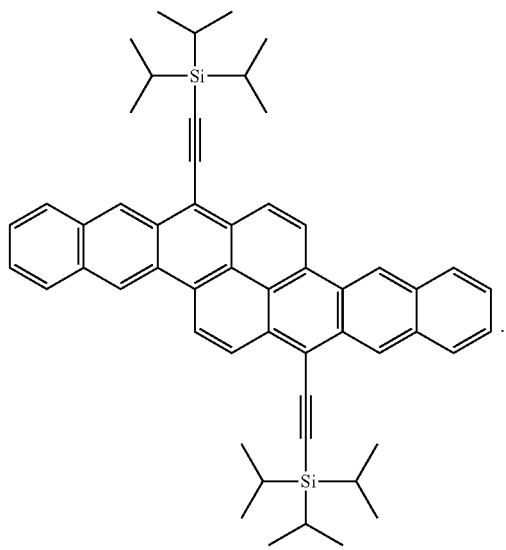 [SMILES: CC(C)[Si](C#Cc1c2cc3ccccc3cc2c2ccc3c(C#C[Si](C(C)C)(C(C)C)C(C)C)c4cc5ccccc5cc4c4ccc1c2c34)(C(C)C)C(C)C]

Another embodiment is a compound according to following structural formula:

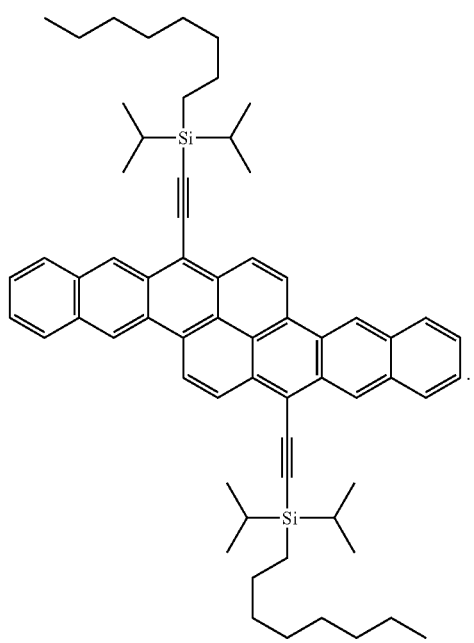 [SMILES: CCCCCCCC[Si](C#Cc1c2cc3ccccc3cc2c2ccc3c(C#C[Si](CCCCCCCC)(C(C)C)C(C)C)c4cc5ccccc5cc4c4ccc1c2c34)(C(C)C)C(C)C]

Another embodiment is a compound according to following structural formula:

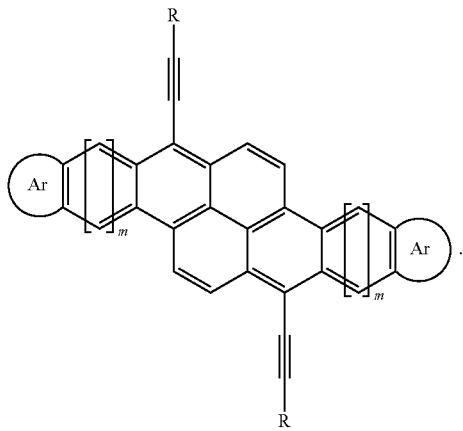

Ar can be an aryl group. In some instances, Ar is an aryl group, with the proviso that Ar is not benzene. In some instances, Ar is benzene, thiophene, thienothiophene, naphthalene, or pyridine In some instances, Ar is thiophene, thienothiophene, or naphthalene.

R can be trimethylsilyl, triethylsiyl, triisopropylsilyl, or N-octyldiisopropylsilyl. In some instances, R can be trimethylsiyl or triethylsiyl.

m is an integer, typically from 1 to 5. In some instances, m is 1. In other instances, m is 2; in other instances, m is 3; in other instances, m is 4; in other instances, m is 5.

In particular embodiments, Ar is thiophene, thienothiophene, naphthalene, or pyridine and R is trimethylsilyl, triethylsilyl, triisopropylsilyl, or N-octyldiisopropylsilyl. In other instances, Ar is benzene, thiophene, thienothiophene, naphthalene, or pyridine and R is trimethylsilyl, triethylsiyl.

Another embodiment is a method of making a compound. The method includes a) contacting Compound 3 with polyphosphoric acid to produce Compound 4; b) contacting Compound 4 with R-silyl acetylene, and n-butyl lithium, wherein R is triisopropyl or N-octyldiisopropylsilyl; and c) contacting the result of b) with $SnCl_2$ in HCl, to thereby yield a compound having the formula:

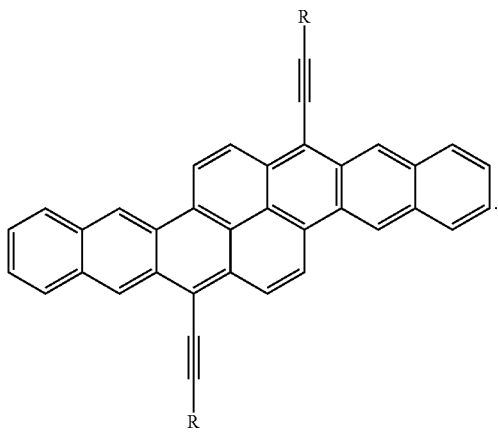

In some instances, the method further includes contacting Compound 2 with KOH in MeOH and THF to yield Compound 3. In some instances, the method further includes contacting Compound 1 with 1, 5-dibromonaphthalene, Pd(0), THF, and potassium carbonate to yield Compound 2. In some instances, the Pd(0) is tetrakis(triphenylphosphine)-palladium (0).

Another embodiment is a method of making a compound. The method includes a) contacting Compound 3 with polyphosphoric acid to produce Compound 4; b) contacting Compound 4A with R-acetylene, and n-butyl lithium, wherein R is triisopropyl or N-octyldiisopropylsilyl; and c) contacting the result of b) with $SnCl_2$ in HCl, to thereby yield a compound having the formula:

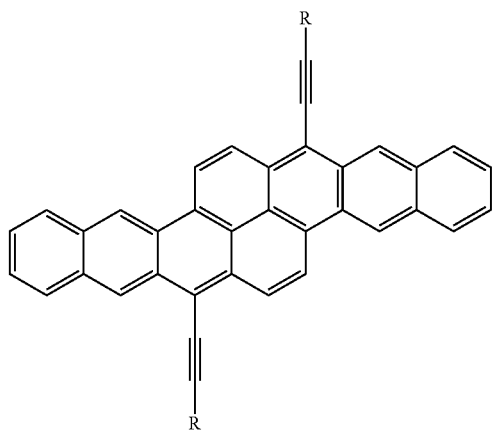

Another embodiment is a method of making a compound. The method includes a) contacting Compound 3A with polyphosphoric acid to produce Compound 4A; b) contacting Compound 4A with R-acetylene, and n-butyl lithium; and c) contacting the result of b) with $SnCl_2$ in HCl, to thereby yield a compound having the formula:

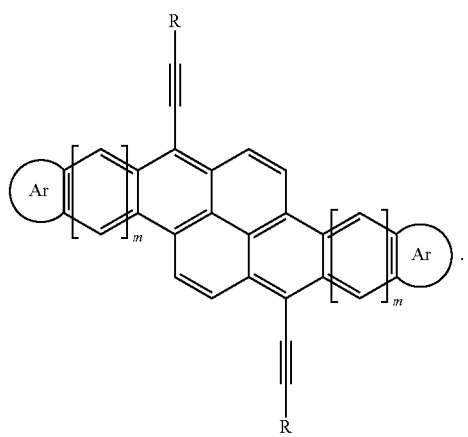

Ar, R, and m are as defined above. In some instances, Ar can be benzene, thiophene, thienothiophene, naphthalene, or pyridine. In some instances, R can be trimethylsiyl, triethylsiyl, triisopropylsilyl, or N-octyldiisopropylsilyl. In some instances, m can be an integer from 1 to 5.

In some instances, the method further includes contacting Compound 2A with KOH in MeOH and THF to yield Compound 3A. In some instances, the further includes contacting Compound 1A with 1, 5-dibromonaphthalene, Pd(0), THF, and potassium carbonate to yield Compound 2A. In some instances, the Pd(0) is tetrakis(triphenylphosphine)-palladium(0).

Another embodiment is a field effect transistor that includes one or more of the compounds described herein. In some instances, the field effect transistor is a single crystal.

The compounds disclosed herein provide improved properties. Because the compounds have a large aspect ratio (length versus width), the π-π interactions predominantly occur along the long axis. The large aspect ratios can permit dense crystal packing (2-D packing), which can provide strong intermolecular interactions between different stacks and lead to high-performance devices. In contrast, compounds having a smaller aspect ratio, such as a ratios closer to 1, crystallize with close-to-cofacial π-π packing (e.g., 1-D packing). For materials with 1-D packing, the distance between the adjacent stacks is usually large and leads to poor connectivity, which results in poor electronic communication and small transfer integrals between stacks. Therefore, these materials exhibit poor mobilities in thin film and single crystal transistors.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4A shows transfer characteristics in the saturated region. FIG. 4B shows output characteristic at different gate voltages. FIG. 4C shows the plot of dependence of mobility versus of gate voltage. FIG. 4D shows device stability test over several months.

FIGS. 7A-C are ultraviolet photoelectron spectra. FIG. 7A is an ultraviolet spectrum of the secondary electron cutoff region. FIG. 7B is an ultraviolet spectrum of the HOMO region. FIG. 7C is an ultraviolet spectrum of the magnified HOMO region of ITO, BT-1 and BT-2.

FIG. 14A shows $^1$HNMR. FIG. 14B shows $^{13}$CNMR.

FIG. 15A shows $^1$HNMR. FIG. 15B shows $^{13}$CNMR.

FIG. 16A shows $^1$HNMR. FIG. 16B shows $^{13}$CNMR.

FIG. 17A shows $^1$HNMR. FIG. 17B shows $^{13}$CNMR.

DETAILED DESCRIPTION OF THE INVENTION

A description of example embodiments of the invention follows.

While this invention has been particularly shown and described with references to example embodiments thereof, it will be understood by those skilled in the art that various changes in form and details may be made therein without departing from the scope of the invention encompassed by the appended claims.

Synthesis of Soluble Bistetracene

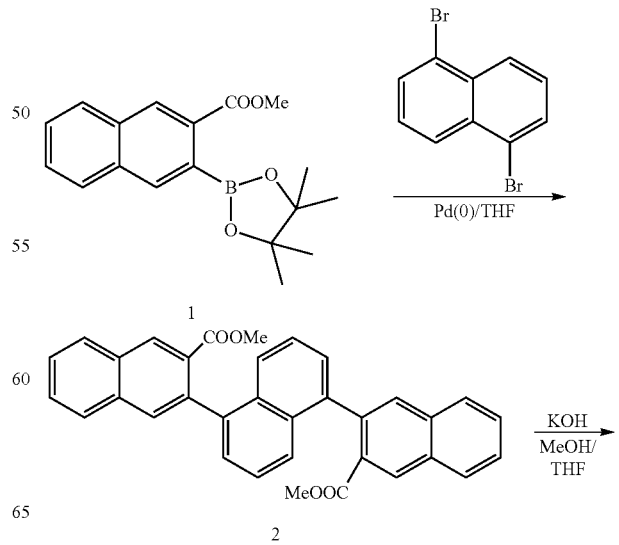

Scheme 1. The synthesis of soluble bistetracene.

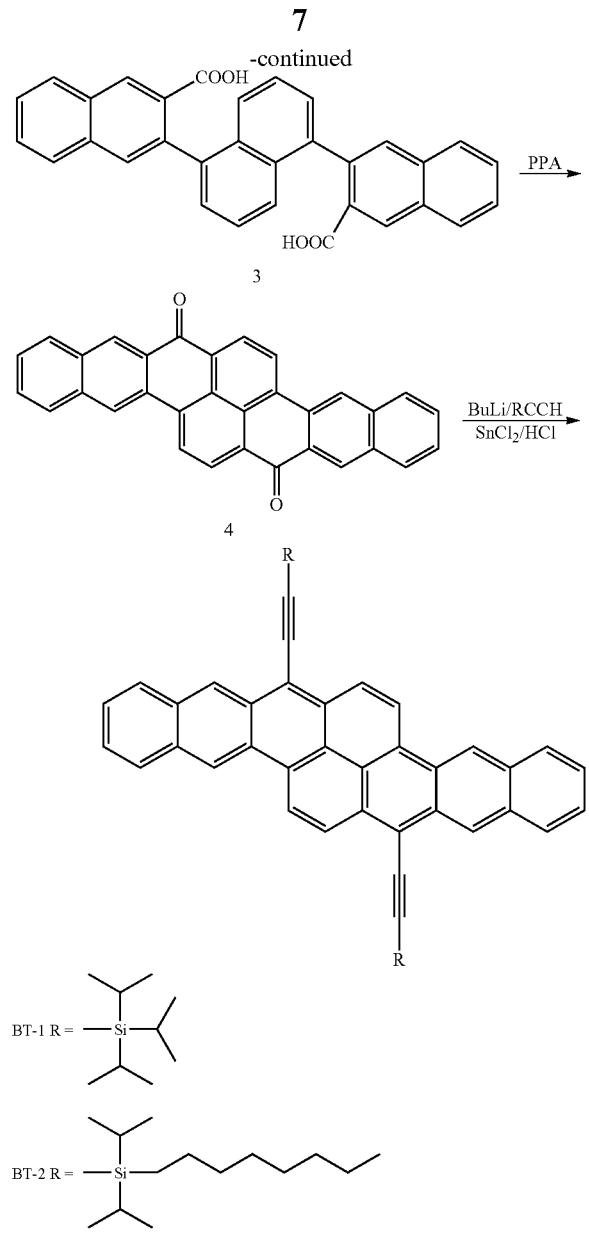

Scheme 1 shows the synthesis of soluble bistetracene. Diketone 4 is a key intermediate compound for soluble bistetracene. In this communication, we develop a modified procedure to synthesize bistetracene quinone with high overall yield. A Suzuki coupling between the boronic ester 1 and 1, 5-dibromonaphthalene produced compound 2, which was subsequently hydrolyzed to a dicarboxylic acid 3 in high yield. The desired diketone 4 was then obtained from 3 under polyphosphoric acid (PPA). Lithiation of alkyl-substituted silylacetylene in THF with BuLi to form its anion and subsequent treatment with diketone 4 gave the relative alcohol derivatives, which was followed by a reductive aromatization with $SnCl_2$, affording the desired products. In our study, BT-1 with triisopropylsilyl acetylene (TIPS) substituent and BT-2 with N-octyldiisopropylsilyl acetylene (NODIPSA) substituents are synthesized. These compounds are purified via silica gel column chromatography and recrystallization from hexane.

Figure 1:
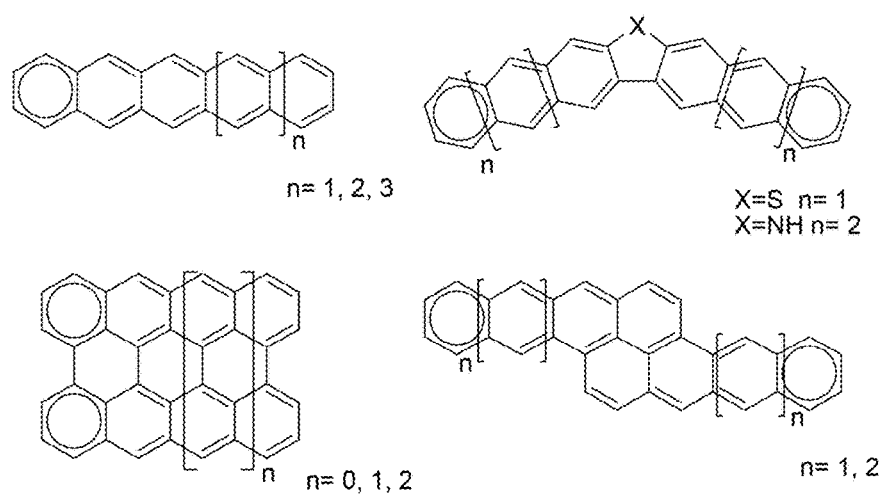
FIG. 1: Chemical structures of representative higher polyacenes with different modes of annellation and Clar sextets.
Figures 2A, 2B:
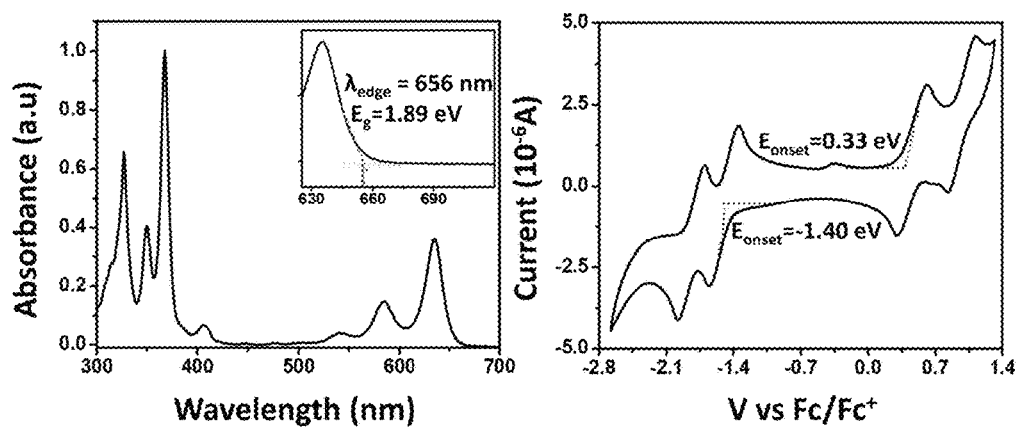
FIG. 2A is the UV-vis absorption spectra of BT-2 in chloroform solution.
FIG. 2B is the cyclic voltammetry of BT-2 in chlorobenzene with TBAPF$_6$ as supporting electrolyte.
Figure 3A:
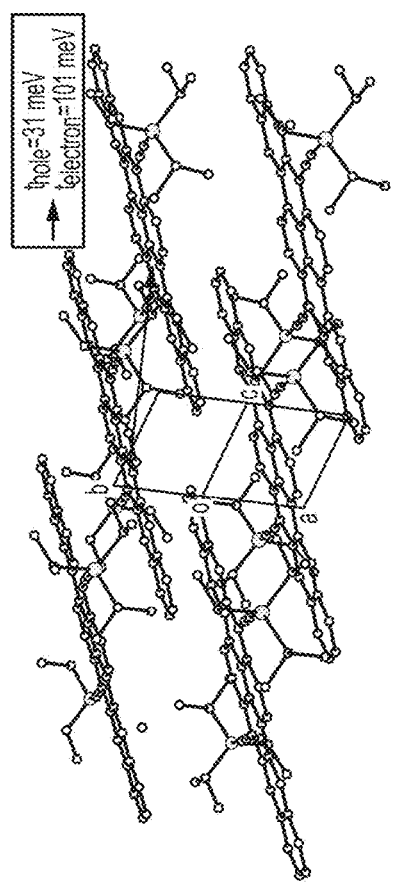
FIGS. 3A and 3B show the crystal structure and molecular packing of BT-1 (slipped 1 D)
Figure 3B:
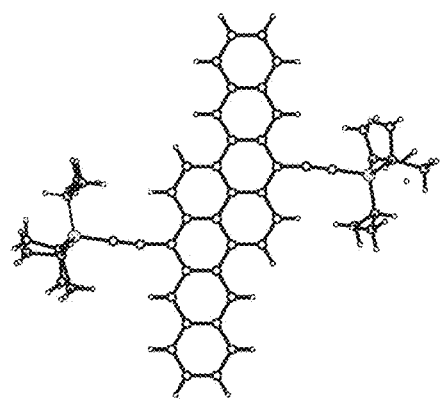
Figure 3C:
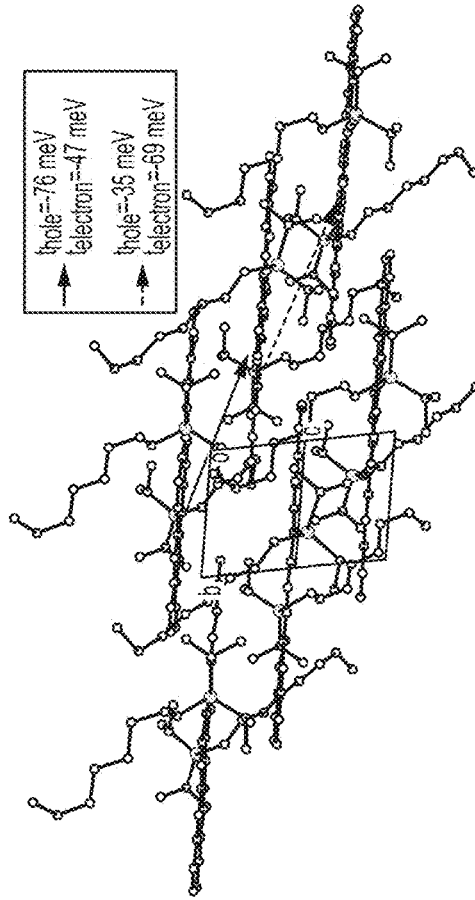
FIGS. 3C and 3D show the crystal structure and molecular packing of BT-2 (interacting 2-D) with indication of the largest calculated electronic couplings.
Figure 3D:
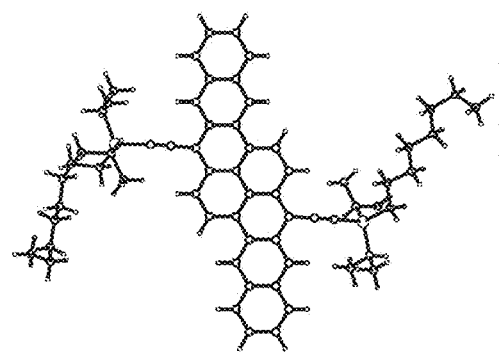

The UV-vis absorption spectra of the compounds were measured in chloroform solution (see FIG. 2A for BT-2). At short wavelengths (up to 550 nm), the compounds show well-defined peaks with intense absorption. The vibronic peaks with weak absorption in the range of 550-635 nm are characteristic of the acene family.[11] The lowest optical band peaks at about 635 nm (1.95 eV). Time-dependent density functional theory (TD-DFT) calculations for BT-1 were performed with the long-range corrected ωB97 functional using the 6-31G** basis set. The range-separation parameter ω was optimized following the ionization potential (IP) tuning procedure.[12] These TD-DFT calculations yield a value of 1.87 eV for the first optical band, which is found to correspond essentially to a HOMO-to-LUMO excitation (see SI for details).

Cyclic voltammetry (CV) studies were performed in chlorobenzene with 0.1 M $TBAPF_6$ as the supporting electrolyte at a scan rate of 100 mV/s and onset oxidation potentials were determined relative to $Fc/Fc^+$ (4.8 eV). The CV of BT-1 and BT-2 exhibit two well-defined, reversible oxidation and reduction waves. The first half-wave reduction-oxidation potentials are −0.76, 1.08 V for BT-1 and −0.77, 1.09 V for BT-2. According to their onset potentials, the IPs and electron affinities (EAs) were estimated at 5.11 and 3.40 eV for compound BT-1 and 5.13 and 3.40 eV for compound BT-2; values comparable to those of TIPS-pentacene.[13] The optical gap extracted from the onsets of the optical spectra is 1.89 eV. DFT calculations also confirm that, as expected, the energies of the frontier orbitals in both systems are nearly identical (see SI). The IPs measured by ultraviolet photoelectron spectroscopy (UPS) (see SI) of BT-1 and BT-2 were 5.02 and 4.88 eV, respectively. Small deviation of IPs between BT-1 and BT-2 (0.14 eV) might be attributed to their different packing motifs in thin film. We also monitored UV-vis absorption over time for compound BT-1 in chloroform and found that it has a half-life time of four days (see SI), which is about 200 times more stable than pentacene.[14] These data thus point out that these compounds are very stable.

The crystal structures of BT-1 and BT-2 were determined by single-crystal X-ray diffraction (FIGS. 3A-D). Both BT-1 and BT-2 crystals are triclinic, space group P$\bar{1}$. Although both structures have two molecules per unit cell, they differ in that the asymmetric unit of BT-1 has two half molecules (sitting on inversion centers), whereas BT-2 has a single whole molecule per asymmetric unit. As shown in FIG. 3, BT-1 exhibits a slipped one-dimensional π-stacking motif, which is similar to that observed for some soluble pentacene derivatives.[15] The interplanar distance in BT-1 is about 3.37 Å, while the center-to-center distance between two adjacent molecules is about 8.98 Å. The peripheral carbon atoms in the one-dimensional stacks of BT-1 are separated by at least 3.8 Å from adjacent stacks, which is larger than the van der Waals radii for adjacent carbon atoms, leading to poor electronic coupling between two adjacent stacks. By changing the substituent to the larger alkyl groups, the π-stacking motif in BT-2 changed to an interacting two-dimensional packing arrangement with close intra-stack contacts of 3.35 Å. A few atoms within the stacks of BT-2 are separated by as little as 3.6 Å allowing non-negligible electronic coupling between adjacent stacks. Due to the presence of two translationally inequivalent molecules (i.e. molecules related by different inversion centers), the stacks in BT-2 are characterized by two alternating intermolecular center-to-center distances of 8.59 Å and 8.01 Å between adjacent molecules. The introduction of long alkyl groups tends to reduce the distance between the different stacks. This is consistent with the stronger intermolecular van der Waals interactions among the longer alkyl groups ("zipper effect") which results in tighter packing in the solid state.[16] The other important observation is the slight twisting of the acene core of BT-2 (torsion angle 4.8°), which likely arises to alleviate strain in crystal packing due to the bulky substituents.

Figure 4A:
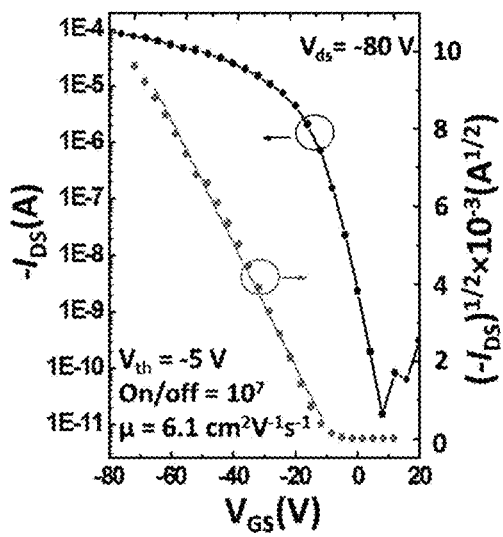
FIGS. 4A-D show single-crystal transistor characteristics of BT-2.
Figure 4B:
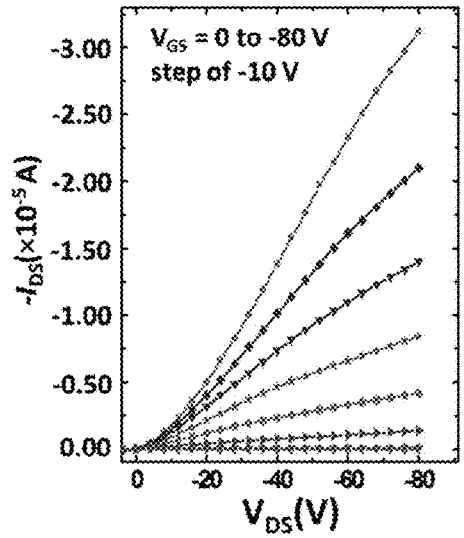
Figure 4C:
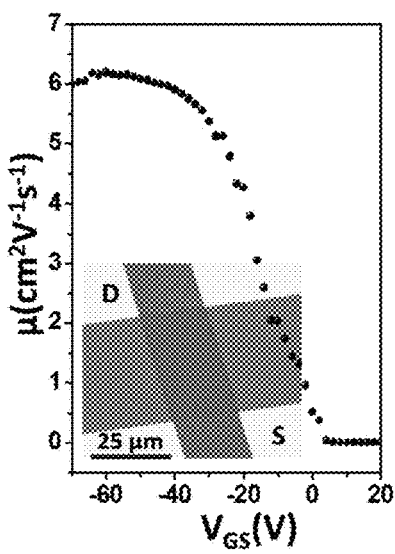
Figure 4D:
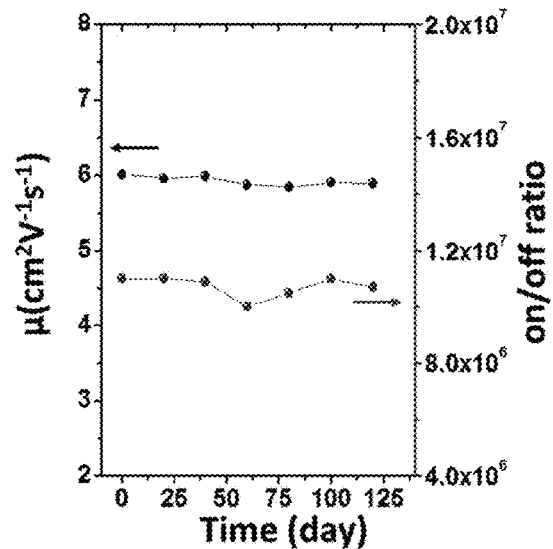

Bottom contact field-effect transistors were fabricated, using a substrate of octadecyl trichlorosilane (ODTS)-treated Si/SiO$_2$. The source and drain electrodes were prepared by gold evaporation, with channel length and width of 50 μm. The OFET devices were measured under ambient conditions using a standard probe station. Transfer and output characteristics are shown in FIGS. 4A and 4B, respectively. The average performance of BT-1 devices was 0.28 cm$^2$ V$^{-1}$ s$^{-1}$, V$_{th}$ of −5 V and current on/off ratios of ~10$^5$. Among the results, the best mobility was 0.4 cm$^2$ V$^{-1}$ s$^{-1}$, with a current on/off ratio of 10$^5$ and threshold of 6 V. However, for BT-2, the average mobility is about 3.90 cm$^2$ V$^{-1}$ s$^{-1}$ with V$_{th}$ of −5 V and current on/off ratios of ~10$^6$ over 10 individual devices. The best mobility is measured to be 6.1 cm$^2$ V$^{-1}$ s$^{-1}$. Thus, BT-2 exhibits excellent device performance, which is higher than that of materials with the similar two-dimensional packing motifs.[1b,1c]

To test the device stability, we prepared single crystal transistors based on compound BT-2 and stored them in laboratory drawers. The devices were periodically tested under ambient conditions for more than 4 months. During this period, only small fluctuations in the mobilities and current on/off ratios were measured.

Figure 5:
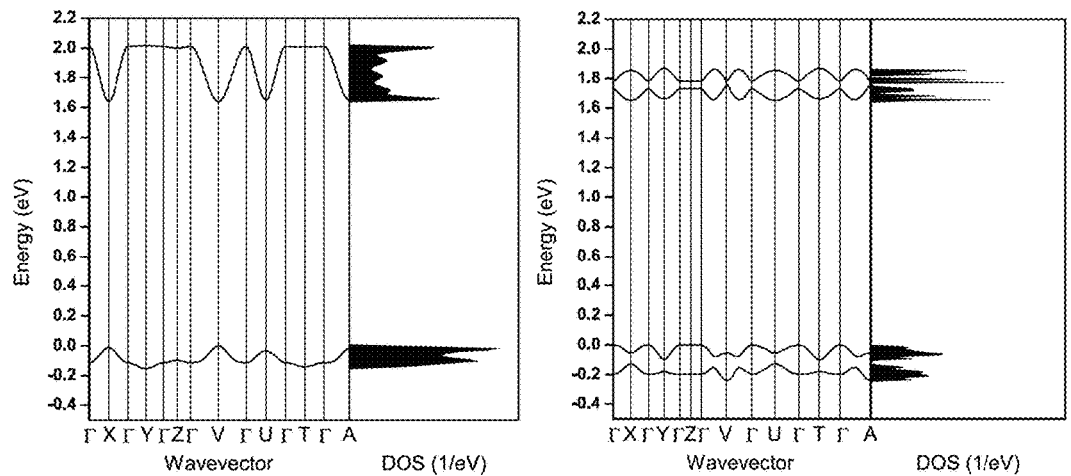
FIG. 5 shows band structure for the relaxed geometry of BT-1 (left) and BT-2 (right). The points of high symmetry in the first Brillouin zone are: Γ=(0, 0, 0), X=(0.5, 0, 0), Y=(0, 0.5, 0), Z=(0, 0, 0.5), V=(0.5, 0.5, 0), U=(0.5, 0, 0.5), T=(0, 0.5, 0.5), A=(0.5, 0.5, 0.5) all in crystallographic coordinates. The zero of energy corresponds to the top of the valence band.

To understand the intrinsic charge transport properties of BT-1 and BT-2, we investigated their electronic band structures via DFT at the B3LYP/6-31G level of theory (FIG. 5). In the case of BT-1, the valence and conduction bandwidths are 0.17 eV and 0.4 eV, respectively. The corresponding transfer integrals for holes and electrons are estimated as 31 meV and 101 meV (FIG. 3B); in the framework of a one-dimensional tight-binding model, such transfer integrals would result in valence and conduction bandwidths of 0.12 eV and 0.4 eV, respectively, in good agreement with those from the periodic boundary conditions calculations. As a consequence of relatively large transfer integrals, the effective masses along the stacking direction are small, 1.07 m$_0$ (m$_0$ is the electron mass in vacuum) for holes and 0.53 m$_0$ for electrons (Table S1). For the sake of comparison we note that the effective masses for holes and electrons in pentacene are 1.60 m$_0$ and 1.45 m$_0$, respectively.[17] Inter-stack electronic couplings were found to be small, i.e. 3 meV and 1 meV for holes and electrons, respectively.

In BT-2, the valence and conduction bands consist of two sub-bands arising from the interaction of the HOMO and LUMO levels, respectively, of the two translationally inequivalent molecules present in the unit cell. The overall valence and conduction bandwidths are estimated to be about 0.22 and 0.20 eV. As a result of two alternating intermolecular distances, the electronic coupling along the stacks is characterized by two transfer integrals, t$_1$ and t$_2$ (−35 meV and −76 meV for holes, and −69 meV and −47 meV for electrons). The band structure calculations yield 1.05 m$_0$ and 0.97 m$_0$, respectively, for hole and electron effective masses along stacking directions. A tight-binding model (but with two sites per unit cell) can be employed to rationalize the band structure for this system as well.[18] According to this model the bandwidths in BT-2 are given by 2(|t$_1$|+|t$_2$|). The tight-binding estimates of 0.22 eV and 0.23 eV for the widths of the valence and conduction bands compare well with the above values derived from band-structure calculations. According to the same tight-binding model the effective masses for charge carriers can be estimated as m$_{eff}$=ℏ$^2$/2t$_{eff}$ d$_{av}$$^2$, where t$_{eff}$=2|t$_1$t$_2$|/(|t$_1$|+|t$_2$|) and d$_{av}$ is the average intermolecular distance along the stack.[18a]

The model yields nearly equal values for the effective transfer integrals for holes and electrons (48 meV versus 55 meV), which explains why both types of carriers in BT-2 possess comparable effective masses. We note that the tight-binding calculations predict for the effective mass of holes in BT-2 a value that is about 30% smaller than in the case of BT-1, which is in contrast with the band-structure calculations showing that the effective masses for holes in both crystals are almost equal. In contrast to BT-1, non-negligible electronic couplings were found between stacks in BT-2, 14 meV and 4 meV for holes and electrons, respectively. Despite a very large difference in the inter-stack electronic couplings, the hole effective masses along the inter-stack direction in both crystals are similar (see SI). This result can be explained by the fact that the effective mass (see above) also depends on the hopping distance; the inter-stack distance in BT-1 is larger than in BT-2. We note, however, that the electronic interaction between stacks, except for holes in BT-2, is expected to be easily diminished by already moderate disorder that is always pre present in actual crystals. Overall, the electronic-structure calculations suggest that BT-1 and BT-2 should exhibit excellent intrinsic charge transport properties for both holes and electrons along the stacking directions. Moderate transport properties are also expected for holes along the inter-stack direction in BT-2.

In summary, we have described a straightforward synthesis of soluble bistetracene derivatives that show attractive properties, such as solution-processability, air stability, low energy band gaps and high carrier mobilities. The OFET measurements and electronic-structure calculations demonstrate that these acenes also exhibit excellent intrinsic charge transport properties. Our study indicates that this annellation mode with an additional Clar sextet significantly increases the stability of this class of extended conjugated semiconductors and, for example, opens new opportunities to explore these materials in mainstream applications such as bulk heterojunction solar cells and large-area, roll-to-roll solution-processable transistors.

Synthesis of Soluble Bisoligoacenes

Scheme 2. The synthesis of soluble bisoligoacenes.

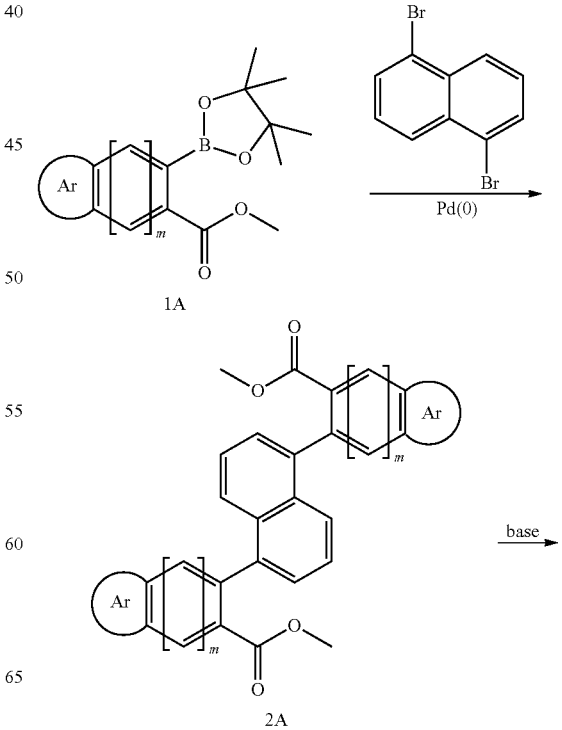

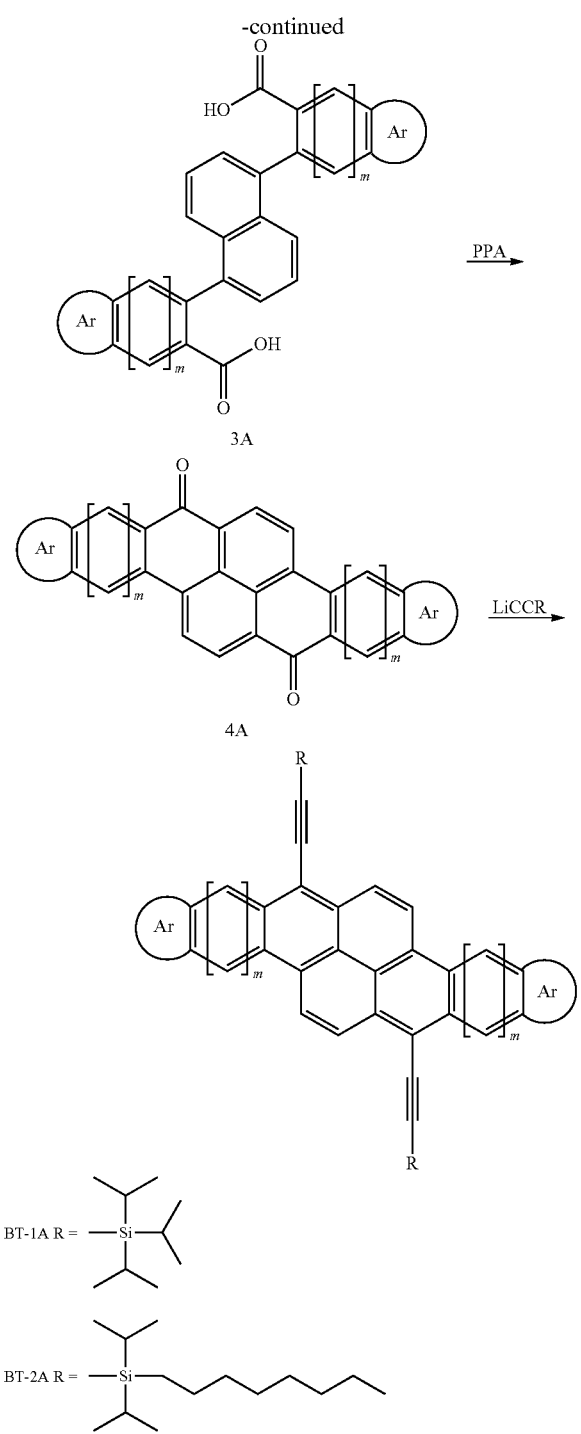

Lithiation of alkyl-substituted silylacetylene in THF with BuLi to form its anion and subsequent treatment with diketone 4A give the relative alcohol derivatives, which is followed by a reductive aromatization with SnCl$_2$, affording the desired products.

Ar is an aryl group. In some instances, Ar is an aryl group, with the proviso that Ar is not benzene. In some instances, Ar is benzene, thiophene, thienothiophene, naphthalene, or pyridine. In some instances, R is thiophene, thienothiophene, or naphthalene.

R is trimethylsiyl, triethylsiyl, triisopropylsilyl, or N-octyldiisopropylsilyl. In some instances, R is trimethylsiyl or triethylsiyl.

m is an integer from 1 to 5. In some instances, m is 1. In other instances, m is 2; in other instances, m is 3; in other instances, m is 4; in other instances, m is 5.

In particular embodiments, Ar is an aryl group, with the proviso that Ar is not benzene, and R is trimethylsiyl, triethylsiyl, triisopropylsilyl, or N-octyldiisopropylsilyl. In other embodiments, Ar is an aryl group, and R is trimethylsiyl or triethylsiyl.

EXEMPLIFICATION

General

Throughout this Exemplification, all references to compound numbers refer to the compounds of Scheme 1.

All starting materials were purchased from commercial sources and used without further purification unless there otherwise stated. THF was dried over sodium benzophenone prior to distillation under argon. $^1$H NMR and $^{13}$C NMR spectra were recorded in deuterated solvent on a Bruker ADVANCE 300 NMR. $^1$H NMR chemical shifts are reported in ppm downfield from tetramethylsilane (TMS) reference using the residual protonated solvent as an internal standard. The UV-vis spectra were measured in chloroform solution. The electrochemical properties of these compounds were investigated by cyclic voltammetry (CV) studies, which were performed under nitrogen in 0.1 M THF/TBAPF$_6$ solutions with a scan rate of 100 mV/s. Compound 1 was synthesized according to the literature.[19]

Scheme 2 shows the synthesis of soluble bisoligoacenes, which proceeds similarly to the synthesis of soluble bistetracene, as described above. Scheme 1 shows the synthesis of soluble bistetracene. Diketone 4A is a key intermediate compound for soluble bisoligoacenes. We describe a modified procedure to synthesize bisoligoacenes quinone with high overall yield. A Suzuki coupling between the boronic ester 1A and 1, 5-dibromonaphthalene produces compound 2, which is subsequently hydrolyzed to a dicarboxylic acid 3A in high yield. The desired diketone 4A is then obtained from 3A under polyphosphoric acid (PPA).

Synthesis of Compound 2

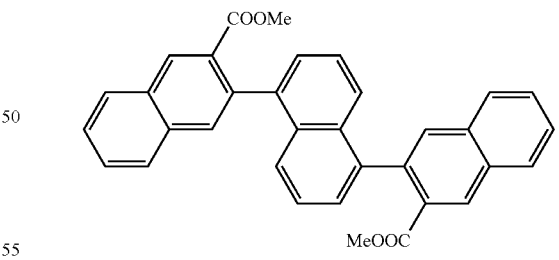

A Schlenk flask was charged with compound 1 (5.6 g, 17.9 mmol), 1,5-dibromonaphthalene (2.3 g, 7.8 mmol), tetrakis(triphenylphosphine)-palladium(0) (700 mg), THF (250 mL), and 2 M potassium carbonate solution (100 mL) under argon. The mixture was heated to 85° C. with vigorous stirring overnight and cooled to room temperature. The organic phase was separated and washed twice with water. After drying over sodium sulfate and filtering, the solvent was removed in vacuo. The residue was purified by column chromatography on silica (Hexane/DCM=1:1) to give a white solid with yield of 75%. $^1$HNMR (CDCl$_3$, 300 MHz):

σ 8.64 (s, 2H), 8.06 (d, 2H), 7.91 (m, 4H), 7.63 (dd, 4H), 7.57 (t, 2H), 7.41 (t, 4H), 3.50 (s, 6H). $^{13}$CNMR (CDCl3, 300 MHz) σ 52.00, 125.21, 125.32, 126.09, 126.16, 126.90, 127.80, 128.47, 128.89, 129.54, 129.88, 130.83, 131.22, 131.34, 131.87, 131.93, 132.25, 132.30, 134.61, 134.67, 137.71, 137.87, 139.81, 140.08, 167.79, 167.95; MALDI-TOF: 496.25. Anal. Calcd for $C_{34}H_{24}O_4$: C, 82.24%; H, 4.87%; Found: C, 82.26; H, 4.85%.

Synthesis of Compound 3

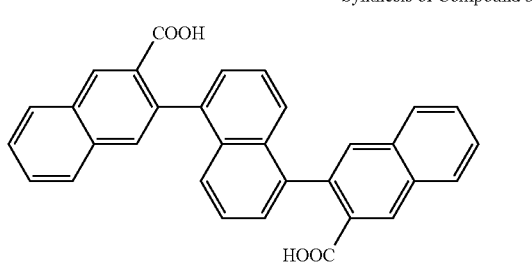

A mixture of compound 2 (3 g, 6.04 mmol), KOH (5.07 g, 90 mmol), THF (100 ml) and methanol (15 ml) was heated at 90° C. for 12 h. After the removal of the solvent, 100 mL of water and 10 ml concentrated hydrochloric acid was added. The formed precipitate was collected by filtration, washed with water, and then dried in vacuum to afford the title product as a white solid with yield of 92%. $^1$HNMR (THF-$d_8$, 300 MHz): σ 8.81 (d, 2H), 8.20 (d, 2H), 8.03 (m, 4H), 7.75 (m, 6H), 7.48 (m, 4H). $^{13}$CNMR (THF-$d_8$, 300 MHz) σ 122.72, 123.29, 123.94, 124.04, 124.64, 125.69, 125.98, 126.08, 126.68, 128.72, 128.96, 129.03, 129.42, 130.23, 130.66, 132.69, 136.36, 138.47, 138.67, 165.44; MALDI-TOF: 468.10. Anal. Calcd for $C_{32}H_{20}O_4$: C, 82.04%; H, 4.30%; Found: C, 82.08; H, 4.32%.

Synthesis of Compound 4

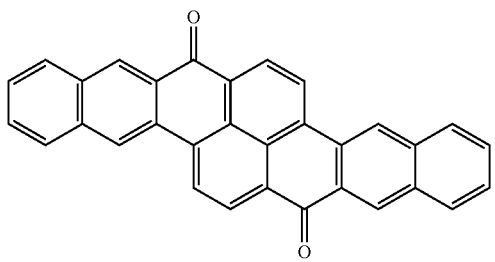

Compound 3 (3.5 g, 7.5 mmol) was added slowly over 2 h to stirred polyphosphoric acid (PPA, 30 mL) at 90° C. under nitrogen atmosphere. The dark brown mixture was further stirred at 120° C. for 3 h. After cooling to room temperature, the mixture was poured into an ice-water mixture (300 mL) with $NaHCO_3$. The precipitate was filtered, washed with water (300 mL) and then methanol, and acetone, and finally dried to give compound 4 as red solid in 93% yield. The product is not soluble for $^1$H and $^{13}$C NMR spectrum and was used directly for next step. MALDI-TOF: 432.30. Anal. Calcd for $C_{32}H_{16}O_2$: C, 88.87%; H, 3.73%; Found: C, 88.91; H, 3.69%.

Synthesis of Compound BT-1

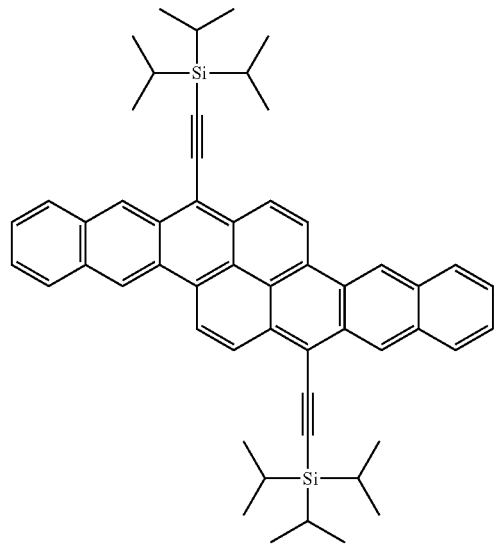

To a solution of triisopropylsilylacetylene (1.27 g, 6.90 mmol) in dry THF (100 ml), 2.7 mL of 2.5M n-BuLi (6.67 mmol) at 0° C. was added dropwise. The solution was allowed to stir for 1 h at 0° C. before the addition of anthanthrene quinone (0.5 g, 1.15 mmol). The mixture was warmed to room temperature and stirred overnight. A solution of $SnCl_2.2H_2O$ (1 g) in 3M HCl (2.5 ml) was added to the solution at room temperature, and it was then stirred for 3 h and then poured into water (500 ml), extracted with chloroform, and dried over $MgSO_4$. The crude product was purified by a short silica chromatographic column (Hexane/dichloromethane 1:1) to provide black, needle-like crystals. Yield: 65%.$^1$HNMR (CDCl$_3$, 300 MHz): σ 9.24 (s, 2H), 8.89 (s, 2H), 8.51 (d, 2H), 8.79 (d, 2H), 8.18 (d, 2H), 7.62 (d, 2H), 7.53 (t, 2H), 7.36 (t, 2H), 1.49 (m, 42H). $^{13}$CNMR (CDCl3, 300) σ 11.87, 19.21, 104.07, 104.95, 112.57, 116.12, 121.57, 122.47, 125.30, 125.58, 126.96, 127.61, 127.89, 128.32, 128.99, 130.85, 130.95, 131.38; MALDI-TOF: 763.11. Anal. Calcd for $C_{54}H_{58}Si_2$: C, 84.98%; H, 7.66%; Found: C, 84.96; H, 7.70%.

Synthesis of Compound BT-2

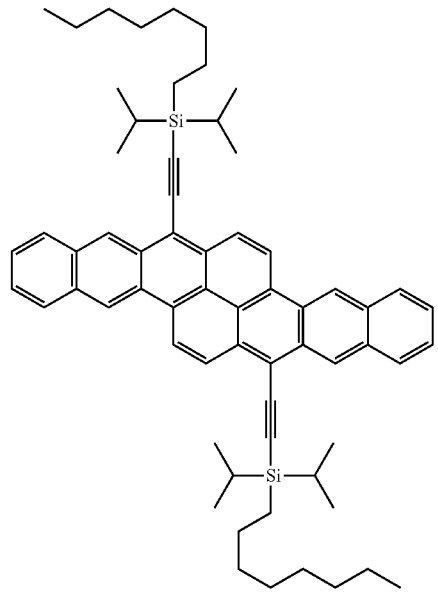

BT-2 was prepared via the same procedure as for compound BT-1. The crude product was purified by a short silica chromatographic column (Hexane) to provide black, belt-like crystals. Yield: 45%. $^1$HNMR (CDCl$_3$, 300 MHz): σ 9.43 (s, 2H), 9.16 (s, 2H), 9.06 (d, 2H), 8.92 (d, 2H), 8.26 (d, 2H), 7.90 (d, 2H), 7.60 (t, 2H), 7.50 (t, 2H), 1.88 (m, 4H), 1.46 (m, 30H), 1.30 (m, 16H), 1.06 (t, 6H), 0.87 (t, 6H). $^{13}$CNMR (CDCl3, 300) σ 10.60, 12.25, 14.14, 18.31, 18.84, 22.72, 25.01, 29.51, 32.04, 34.12, 104.58, 112.57, 116.55, 121.57, 123.50, 125.69, 125.86, 127.52, 127.79, 128.19, 128.45, 130.85, 130.29, 131.49; MALDI-TOF: 902.40. Anal. Calcd for $C_{64}H_{78}Si_2$: C, 85.08%; H, 8.70%; Found: C, 85.11; H, 8.67%.

UV and CV Spectra of BT-1

Figures 6A, 6B:
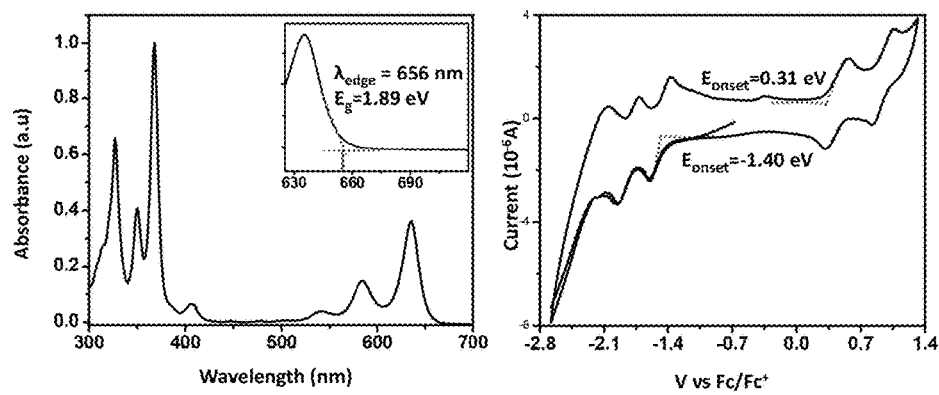
FIG. 6A is a UV-vis absorption spectrum of BT-1 in chloroform solution.
FIG. 6B is a CV of BT-1 in chlorobenzene with TBAPF6 as supporting electrolyte.

UV-vis spectrum was performed in chloroform solution at room temperature. Cyclic voltammograms (CVs) were recorded on a 1000B model electrochemical workstation using glassy carbon discs as the working electrode, Pt wire as the counter electrode, Ag/Ag$^+$ electrode as the reference electrode, and ferrocene/ferrocenium as an internal potential marker. 0.1 M tetrabutylammonium hexafluorophosphate (TBAPF$_6$) dissolved in chorobenzene was employed as the supporting electrolyte. Results are show in FIGS. 6A-B.

Ultraviolet Photoelectron Spectroscopy (UPS) Measurement of the Thin Films of BT-1 and BT-2

UPS measurement was performed using an Omicron SPHERA hemispherical analyzer and a He I (21.22 eV) excitation light source. To obtain the secondary electron cut off (SEC), a sample bias of −3 V was applied in the normal emission geometry. ITO-coated glass was used for the substrate. Prior to the BT-1 and BT-2 film deposition, ITO-coated glass substrates were UV-ozone treated for 15 min. BT-1 and BT-2 were spun-cast with a solution of the concentration of 2 mg ml$^{-1}$ in chloroform with 500 rpm for 5 sec and then 2000 rpm for 55 sec. From the SEC region spectra, the work function of UV-ozone treated ITO was measured by 4.68 eV, while that of BT-1 and BT-2 was measured by 4.47 and 4.12 eV. From the magnified HOMO region (FIG. SXc), the HOMO onset of BT-1 and BT-2 was measured by 0.55 eV and 0.76 eV. Therefore, the ionization energy (=WF+HOMO) of BT-1 and BT-2 was evaluated by 5.02 and 4.88 eV, respectively. On the other hand, overall shape of density of states of BT-1 and BT-2 are quite similar except somewhat difference of the energetic position, which implies that the substituent group does not significantly contribute to its valence electronic structure. Results are shown in FIGS. 7A-C.

X-ray Crystallographic Structure Determination

Figure 8A:
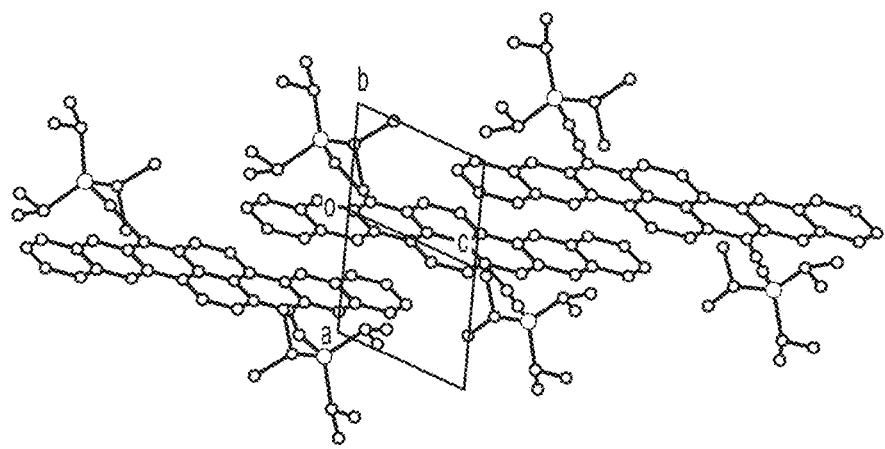
FIG. 8A shows crystal packing of BT-1.
Figure 8B:
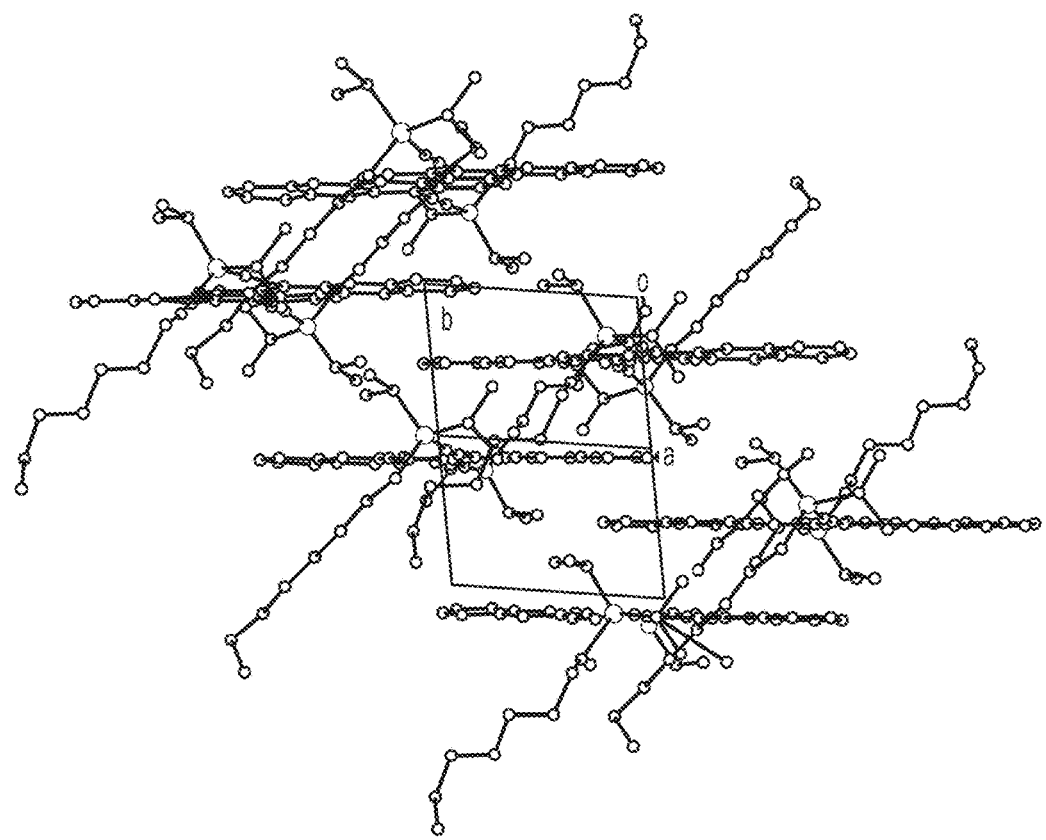
FIG. 8B shows crystal packing of BT-2.

X-Ray crystallographic data were collected with a Bruker-Nonius X8-Proteum rotating anode based diffractometer, using graded multilayer focused CuK radiation (λ=1.54178 Å). Data were collected at 90 K and the structures were solved by direct methods and refined by full-matrix least-squares on F$^2$. The computations were performed using the SHELX-97 programs. Hydrogen atoms were placed at calculated positions and refined using a riding model. Results are shown in FIGS. 8A-B.

Crystal data for BT-1: $C_{54}H_{58}Si_2$: 763.18, space group P-1, a=8.9841(11) Å, b=9.7368(16) Å, c=13.5100(2) Å, α=75.340(14)°, β=70.337(13)°, γ=90.051(14)°, V=1071.9 (3) Å$^3$, Z=1, 3053 reflections collected, the final R was 0.0782, and wR was 0.2496.

Crystal data for BT-2: $C_{64}H_{78}Si_2$: 903.44, space group P-1, a=11.7625(3) Å, b=12.8916(3)Å, c=18.7532(4)Å, α=97.595(2)°, β=106.386(1)°, γ=95.691(2)°, V=2676.27 (11)Å$^3$, Z=2, 9738 reflections collected, the final R was 0.0521, and wR was 0.1608.

Computational Methodology

Figure 9:
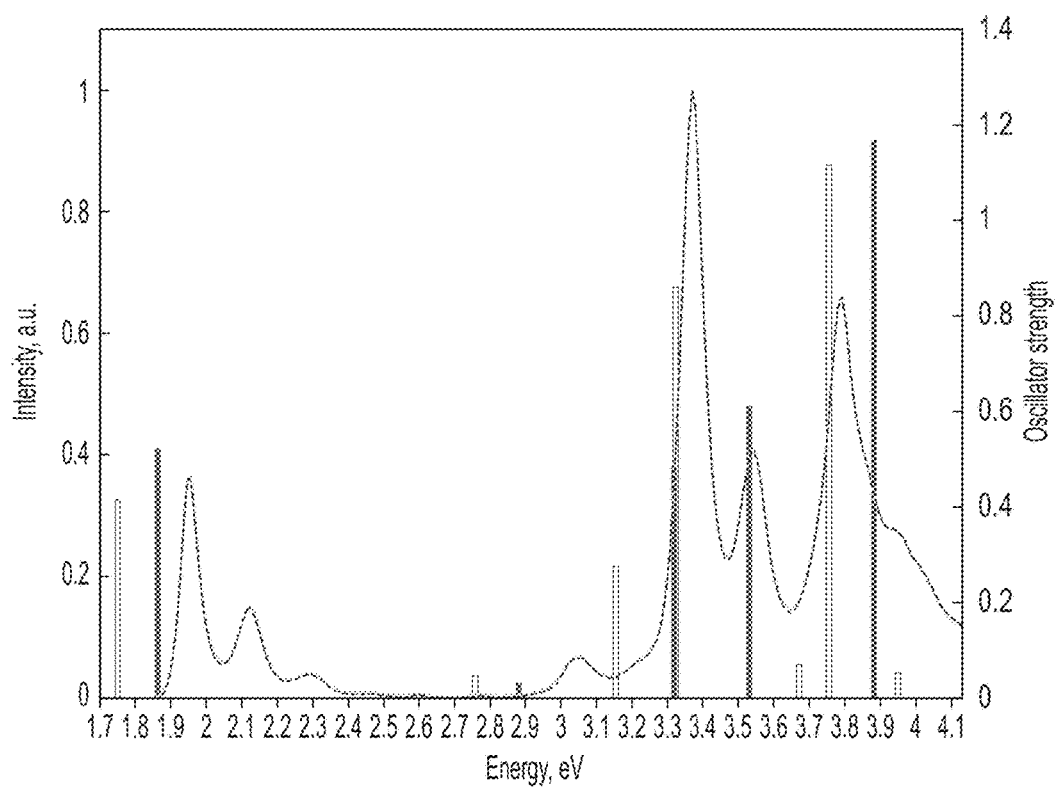
FIG. 9 shows experimental absorption spectra of BT-1 (green solid line) and BT-2 (blue dashed line) with transitions energies and oscillator strengths for the lowest-lying excited states obtained from B3LYP/6-31G (open black bars) and ωB97/6-31G (red bars) calculations for BT-1.
Figure 10:
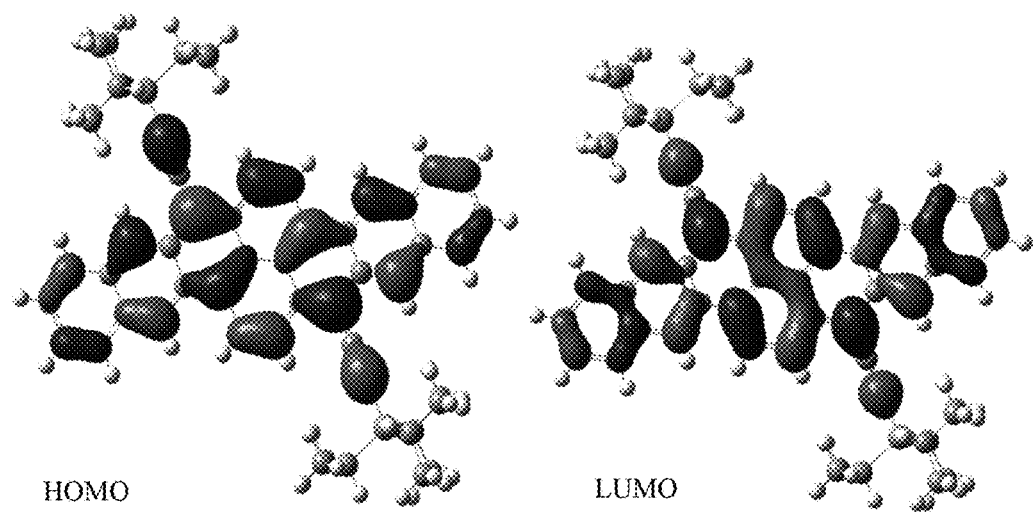
FIG. 10 shows frontier molecular orbitals of BT-1 predominantly involved in the $S_0 \rightarrow S_1$ optical transition at the ωB97/6-31G** level.
Figure 11:
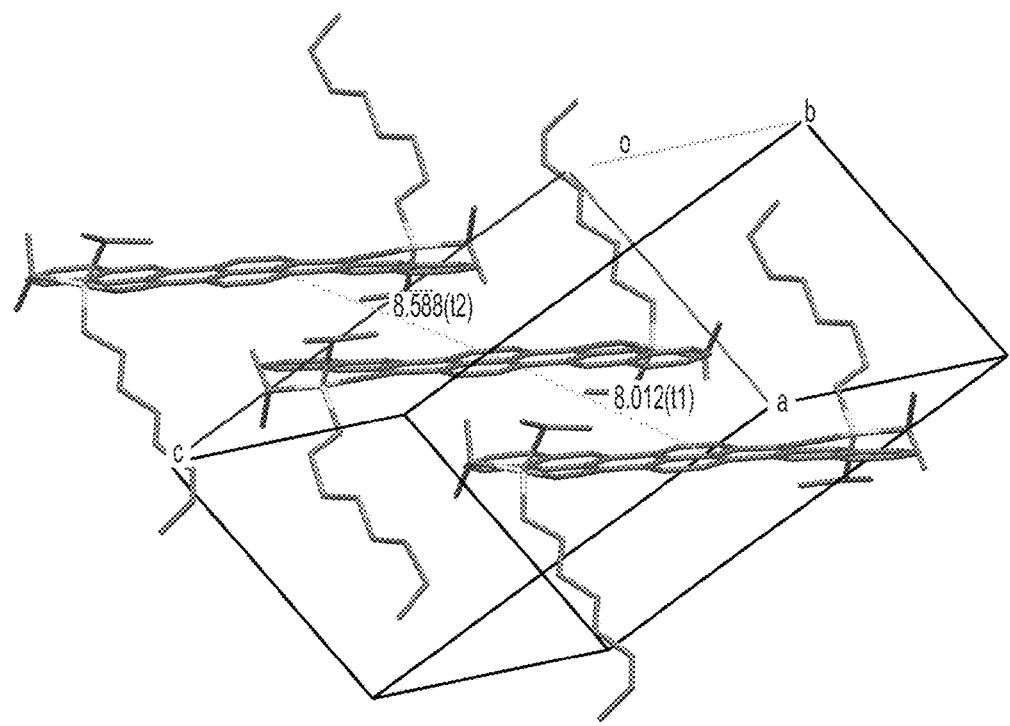
FIG. 11 shows slipped-stack structure of BT-2 showing two inter-dimer distances (in Å) and corresponding to the transfer integral notations t1 and t2.

The electronic band structure and density of states (DOS) were calculated using the crystal geometries of BT-1 and BT-2. These calculations were performed at the B3LYP/6-21G level with the CRYSTAL09 package.[20] Uniform 6×6×4 and 4×4×4 k-point Γ-point centered meshes were employed for BT-1 and BT-2, respectively. The inverse effective mass tensor was calculated from the band structure using finite difference method on a five-point stencil. Subsequent diagonalization of $m_{ij}^{-1}$ provides the principal components and their orientations. Electronic couplings (transfer integrals) for molecular dimers, extracted from the crystal structure, were evaluated using the fragment molecular orbital (FMO) approach[21] as implemented in the NWChem development version[22] at the B3LYP/6-31G level. Excited-state molecular calculations were performed using Gaussian09.[23] Excited states calculations for BT-1 were performed on the optimized "gas-phase" geometry, using both the B3LYP and IP-tuned[24] ωB97[25] functionals (with the ω value in the latter case equal to 0.141 bohr$^{-1}$) and the 6-31G basis set. Results are shown in Tables S1 and S2 and FIGS. 9, 10, and 11.

TABLE S1

Hole and electron effective masses in the units of the electron mass at rest ($m_0$) at the band extrema. Step-size for numerical differentiation was set to 0.01 (1/Bohr).

|  |  | $m/m_0$ | directions |
|---|---|---|---|
| BT-1 | holes at V | 1.074 | a + 0.132b − 0.088c |
|  | (0.5, 0.5, 0) | 4.511 | c − 0.424a + 0.370b |
|  |  | 28.116 | b + 0.023a − 0.386c |
|  | electrons at X | 0.530 | a − 0.010b − 0.016c |
|  | (0.5, 0, 0) | 9.412 | c − 0.469a − 0.014b |
|  |  | Inf. | b + 0.112a − 0.199c |
| BT-2 | holes at Γ | 1.054 | b + 0.488a + 0.001c |
|  | (0, 0, 0) | 5.259 | a − 0.337b − 0.018c |
|  |  | 110.134 | c + 0.508a + 0.222b |
|  | electrons at X | 0.969 | b + 0.860a − 0.001c |
|  | (0.5, 0, 0) | 22.400 | a − 0.720b − 0.075c |
|  |  | 280.434 | c + 0.572a + 0.170b |

TABLE S2

UPS, Electrochemical and Optical data for BT-1 and BT-2.

| Compd | UPS IP | Electrochemical[a] | | | | | | | Optical[b] | |
|---|---|---|---|---|---|---|---|---|---|---|
| | | $E(A^+/A)$ | $E(A^{2+}/A^+)$ | $E(A^-/A)$ | $E(A^{2-}/A^-)$ | IP | EA | $E_{gap}$ | $\lambda_{max}$ | $E_{opt}$ |
| BT-1 | 5.02 | 1.08 | 1.60 | −0.76 | −1.18 | 5.13 | 3.40 | 1.73 | 656 | 1.89 |
| BT-2 | 4.88 | 1.09 | 1.62 | −0.77 | −1.16 | 5.11 | 3.40 | 1.71 | 656 | 1.89 |

[a]Cyclic voltammetry (CV) studies were performed in chlorobenzene as 0.1M TBAPF$_6$ as the supporting electrolyte at a scan rate of 100 mV/s and E is the half-wave potential (E$_{1/2}$) for reversible processes vs Ag/Ag$^+$; IP, EA, and E$_{gap}$ were determined from the onset of the first oxidation and the first reduction waves in cyclic voltammograms, relative to Fe/Fe$^+$ (4.8 eV).
[b]Spectra were obtained in CHCl$_3$ and wavelengths are in nm. E$_{opt}$ is the optical gap evaluated from the onset of the first optical band.

Device Fabrication

Figure 12A:
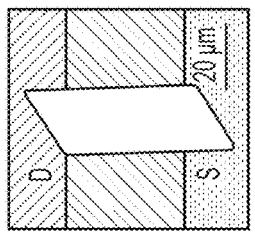
FIG. 12A show a single-crystal transistor of BT-1.
Figure 12C:
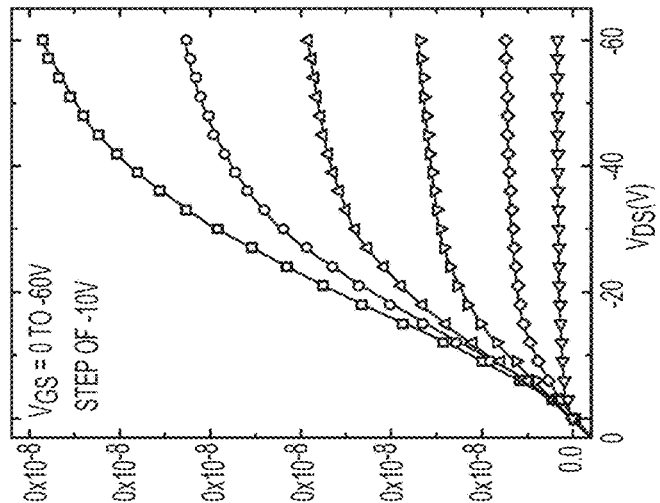
FIG. 12C shows output characteristic at different gate voltages of BT-1.
Figure 12B:
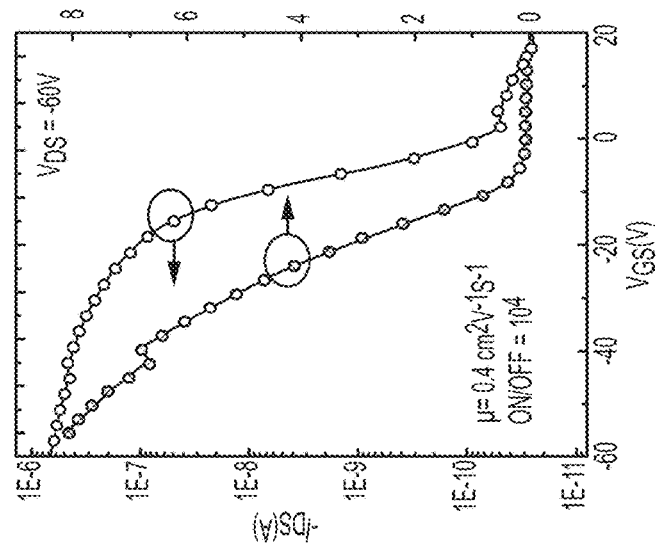
FIG. 12B shows characteristics in the saturated region at a drain voltage of −60 V.
Figure 13A:
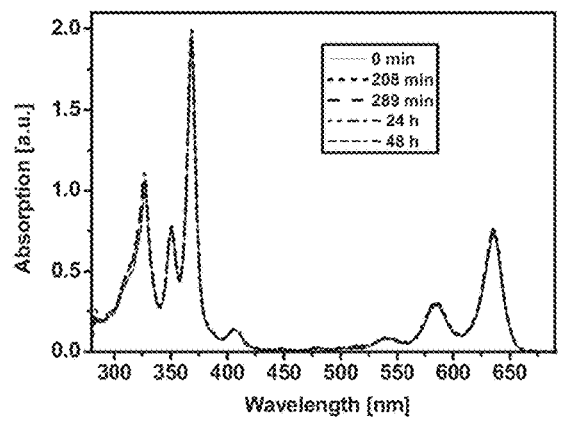
FIG. 13A shows monitored UV-vis absorption over time in Toluene.
Figure 13B:
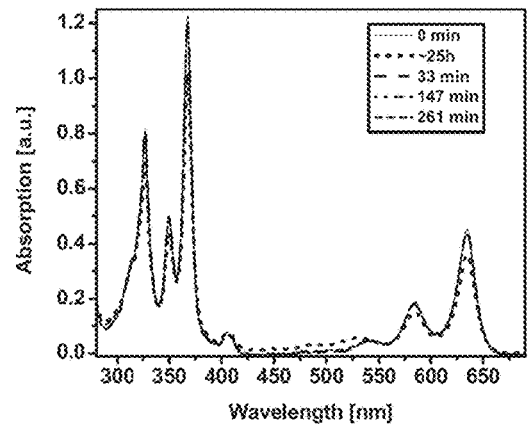
FIG. 13B shows monitored UV-vis absorption over time in Chloroform.
Figure 13C:
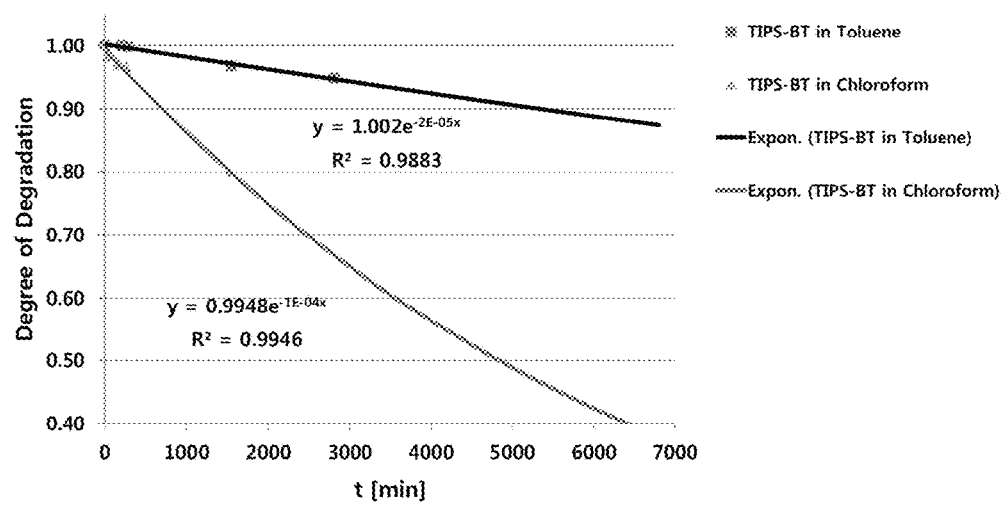
FIG. 13C shows degree of degradation of BT in different solvents vs time.
Figure 14A:
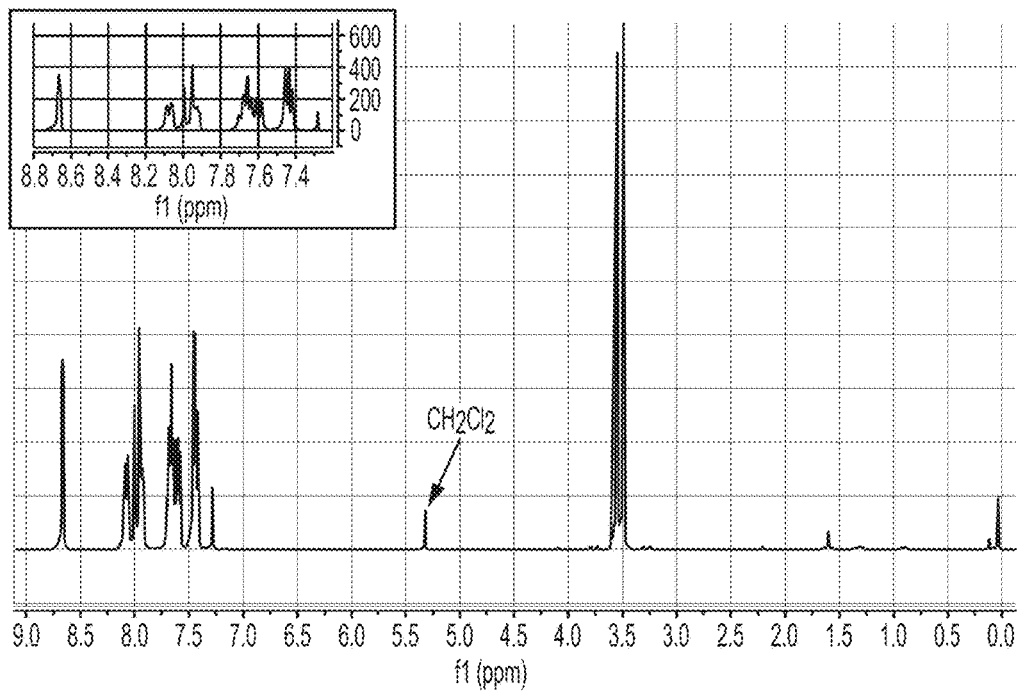
FIGS. 14A-B show NMR spectra of compound 2 at room temperature (CDCl$_3$).
Figure 14B:
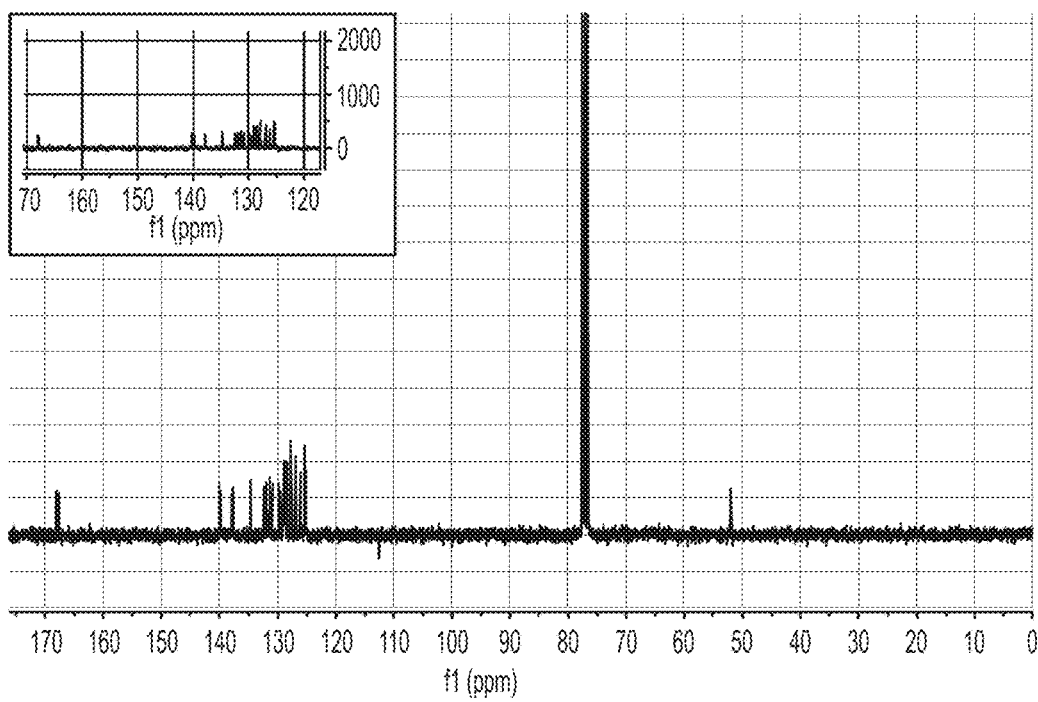
Figure 15A:
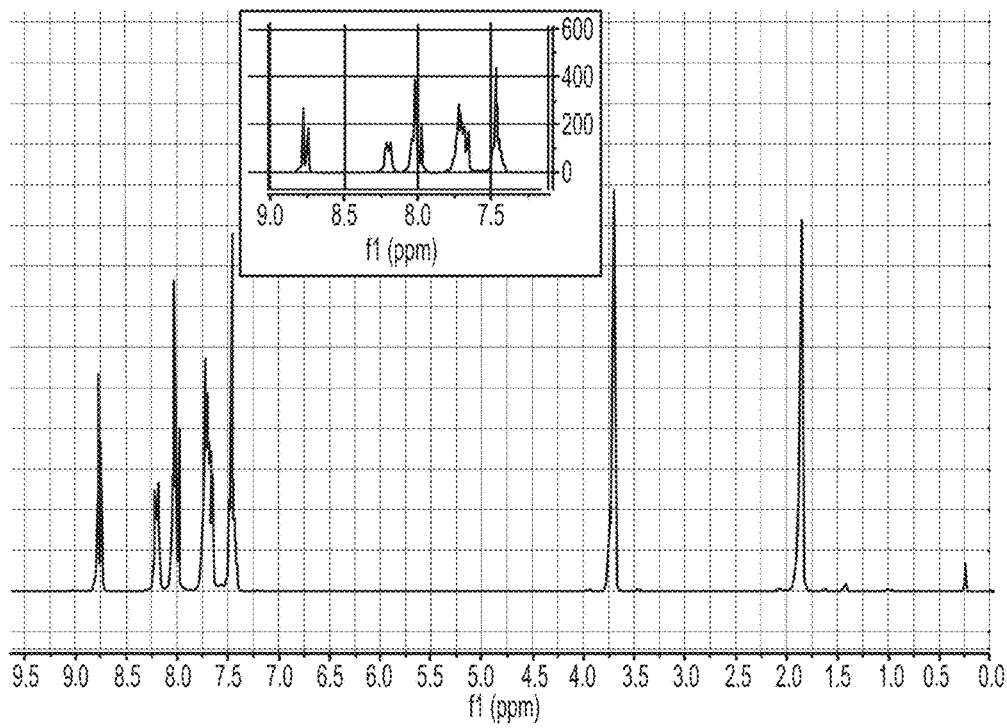
FIG. 15A-B show NMR spectra of compound 3 at room temperature (THF-d$_8$).
Figure 15B:
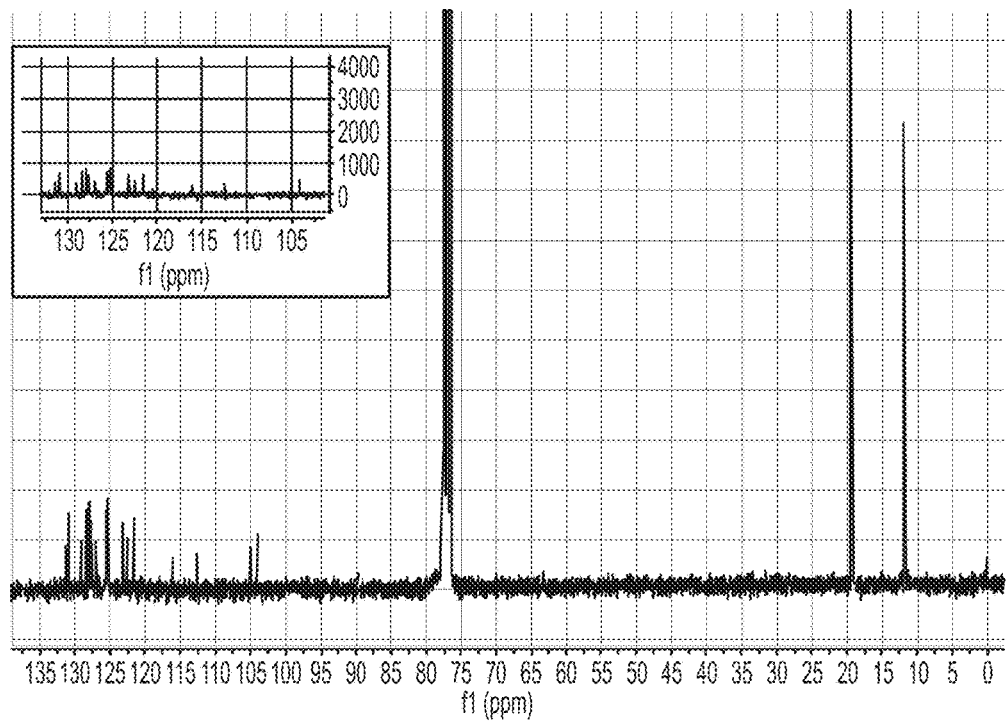
Figure 16A:
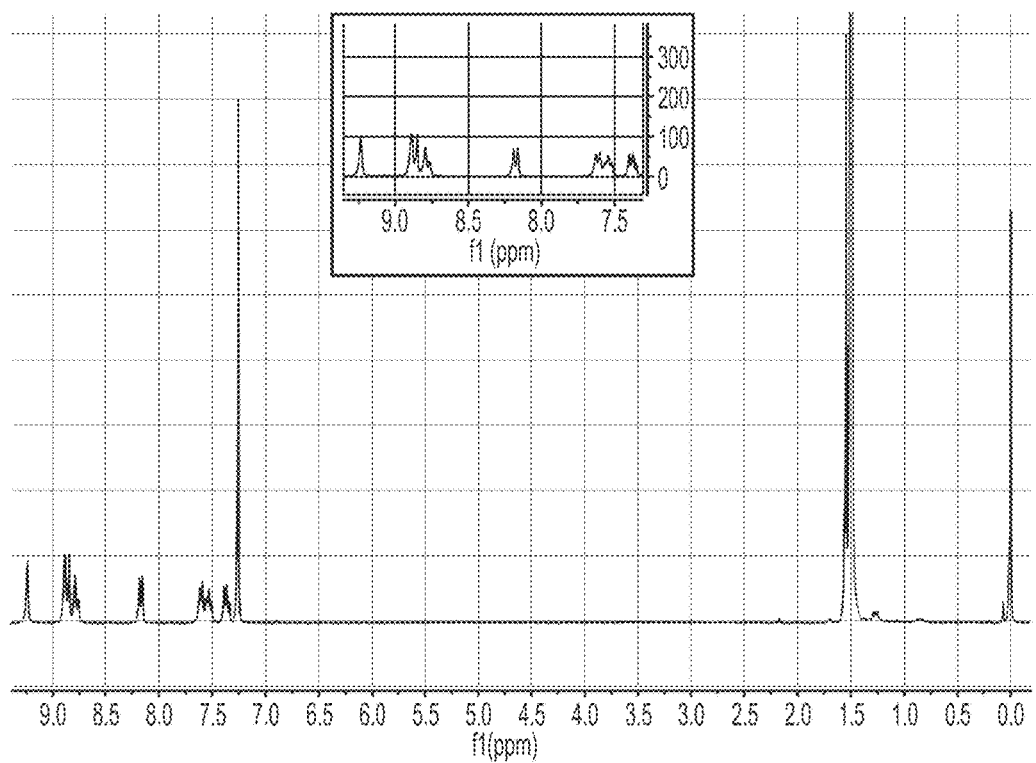
FIGS. 16A-B show NMR spectra of compound BT-1 at room temperature (CDCl$_3$).
Figure 16B:
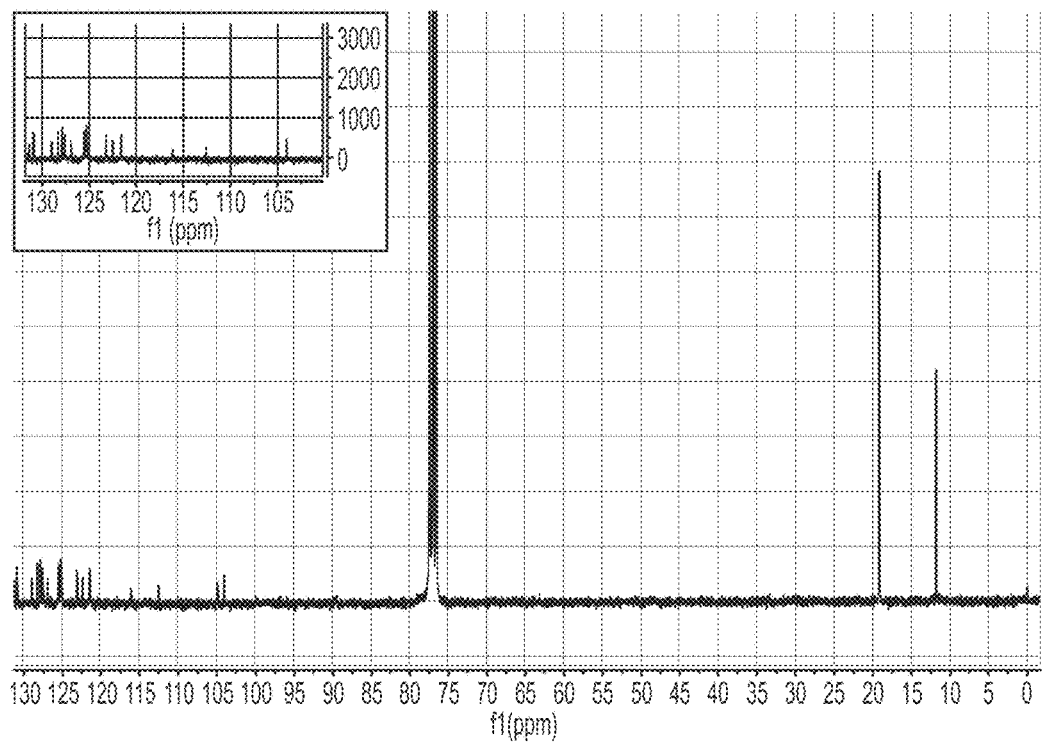
Figure 17A:
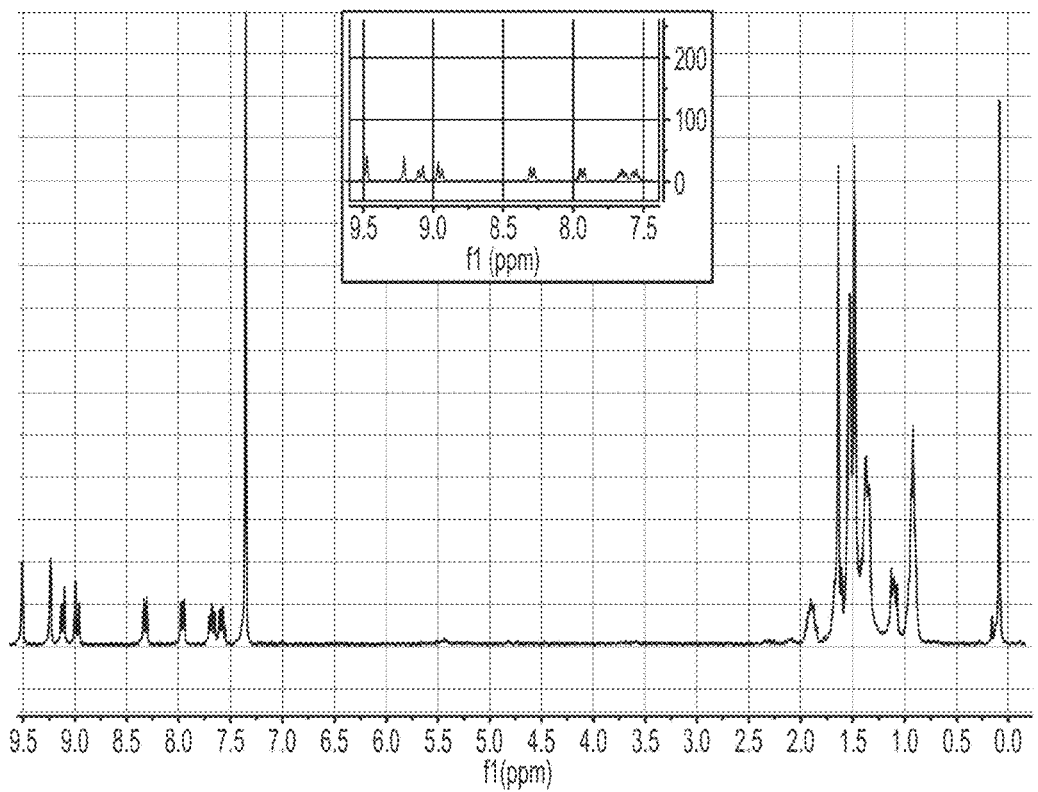
FIGS. 17A-B show NMR spectra of compound BT-2 at room temperature (CDCl$_3$).
Figure 17B:
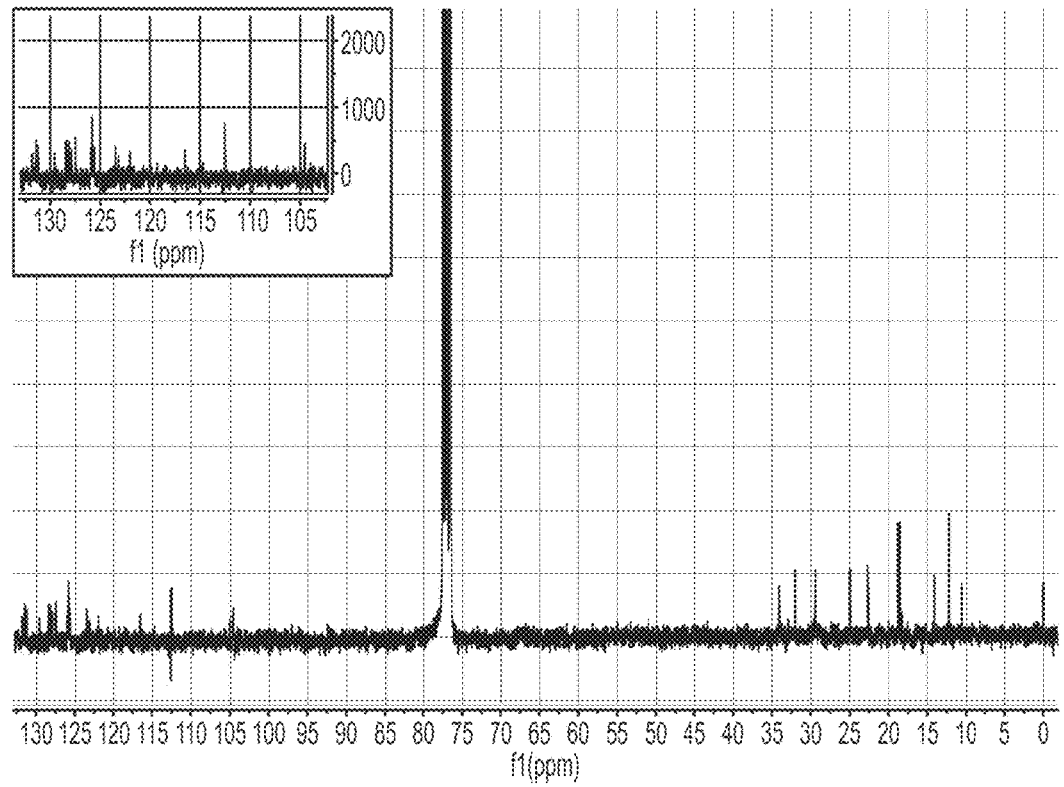

FET devices were fabricated in the bottom-gate, bottom-contact geometry configuration. FETs with were fabricated on highly doped Si gate contact, with a 200 or 300 nm thermally grown SiO$_2$ gate dielectric and 5 nm Cr/45 nm Au source and drain contacts defined by photolithography at channel lengths of 50 μm, and deposited by e-beam evaporation. These substrates were cleaned with H$_2$SO$_4$ and H$_2$O$_2$, and then treated by OTS. For BT-1 device, a 0.5 wt % solution of the BT-1 in toluene was dropped over the substrates and additional solvent was placed around the substrates in a Petri dish with a closed lid to ensure a slow evaporation rate. For BT-2, the crystal was formed in acetone and then was spin coated on the substrate. FET characteristics were obtained at room temperature in air on a Keithley 4200 SCS and Micromanipulator 6150 probe station. The mobility of the devices was calculated in the saturation regime. The equation is listed as follows:

$$I_{DS} = (W/2L)C_i\mu(V_{gs}-V_T)^2$$

where W/L is the channel width/length, $C_i$ is the insulator capacitance per unit area, and $V_{GS}$ and $V_T$ are the gate voltage and threshold voltage, respectively. Results are shown in FIGS. 12A-C and Table S3.

TABLE S3

Charge transport characteristics of the bistetracenes.

| | Effective mass (m$_0$) | | Mobility[a] (cm$^2$V$^{-1}$s$^{-1}$) | | |
|---|---|---|---|---|---|
| Compd | m$_{Hole}$ | m$_{El}$ | μ$_{ave}$ | μ$_{max}$ | Ion/Ioff |
| BT-1 | 1.07 | 0.53 | 0.28 ± 0.10 | 0.40 | 10$^6$ |
| BT-2 | 1.05 | 0.97 | 3.88 ± 1.40 | 6.10 | 10$^7$ |

[a]Bottom contact single-crystal transistors and the average mobility were calculated from at least 10 devices Results are shown in FIGS. 13A-C, 14A-B, 15A-B, 16A-B, and 17A-B and Table S4.

TABLE S4

Left: Decay of BT-1 in chloroform (half time life: 4.8 days), and right: Decay of BT-1in toluene (half time life: 9.7 days).

| Time (min) | Degree of Degradation | Time (min) | Degree of Degradation |
|---|---|---|---|
| 0 | 1.00 | 0 | 1.00 |
| 33 | 0.98 | 208 | 1.00 |
| 147 | 0.97 | 289 | 1.00 |
| 263 | 0.97 | 1544 | 0.97 |
| 1531 | 0.80 | 2807 | 0.95 |

REFERENCES (1) (a) Bendikov, M.; Wudl, F.; Perepichka, D. F. Chem. Rev. 2004, 104, 4891. (b) Anthony, J. E. Angew. Chem., Int. Ed. 2008, 47, 452. (c) Anthony, J. E. Chem. Rev. 2006, 106, 5028. (d) Clar, E. Polycyclic Hydrocarbons; Academic Press: New York, 1964; Vol. 1.
(2) (a) Zade, S.; Bendikov, M. Angew. Chem., Int. Ed. 2010, 49, 4012. (b) Winkler, M.; Houk, K. N. J. Am. Chem. Soc. 2007, 129, 1805-1815.
(3) (a) Sun, Z.; Ye, Q.; Chi, C.; Wu, J. Chem. Soc. Rev. 2012, 41, 7857. (b) Jiang, D. F.; Dai, S. Chem. Phys. Lett. 2008, 466, 72-75.
(4) (a) Mondal, R.; Tönshoff, C.; Khon, D.; Neckers, D. C.; Bettinger, H. F. J. Am. Chem. Soc. 2009, 131, 14281-14289. (b) Ehrlich, S.; Bettinger, H. F.; Grimme, S. Angew. Chem., Int. Ed. 2013, 52, 10892-10895. (c) Tonshoff, C.; Bettinger, H. F. Angew. Chem., Int. Ed. 2010, 49, 4125-4128. (d) Watanabe, M.; Chen, K.; Chang, Y. J.; Chow, T. J. Acc. Chem. Res. 2013, 46, 1606-1615. (e) Zade, S. S.; Zamoshchik, N.; Reddy, A. R.; Fridman-Marueli, G.; Sheberla, D.; Bendikov, M. J. Am. Chem. Soc. 2011, 133, 10803-10816.
(5) (a) Payne, M. M.; Parkin, S. R.; Anthony, J. E. J. Am. Chem. Soc. 2005, 127, 8028-8029. (b) Chun, D.; Cheng, Y.; Wudl, F. Angew. Chem. Int. Ed. 2008, 47, 8380-8385. (c) Kaur, I.; Stein, N. N.; Kopreski, R. P.; Miller, G. P. J. Am. Chem. Soc. 2009, 131, 3424-3425. (d) Purushothaman, B.; Bruzek, M.; Parkin, S. R.; Miller, A.; Anthony, J. E. Angew. Chem., Int. Ed. 2011, 50, 7013-7017. (e) Xiao, J. C.; Duong, H. M.; Liu, Y.; Shi, W. X.; Li, G.; Li, S. Z.; Liu, X. W.; Ma, J.; Wudl, F.; Zhang, Q. C. Angew. Chem. Int. Ed. 2012, 51, 6094-6098.
(6) (a) Watanabe, M.; Chang, Y. J.; Liu, S. W.; Chao, T. H.; Goto, K.; Islam, M. M.; Yuan, C. H.; Tao, U. T.; Shinmyozu, T.; Chow, T. J. Nat. Chem. 2012, 4, 574-578. (b) Purushothaman, B.; Parkin, S.; Kendrick, M. J.; David, D.; Ward, J. W.; Yu, L.; Stingelin, N.; Jurchescu, O. D.; Ostroverkhova, O.; Anthony, J. E. Chem. Commun. 2012, 48, 8261-8263. (c) Winzenberg, K. N.; Kemppinen, P.; Fanchini, G.; Bown, M.; Collis, G. E.; Forsyth, C. M.; Hegedus, K.; Birendra Singh, T.; Watkins, S. E. Chem. Mater. 2009, 21, 5701-5703.
(7) (a) Gutzler, R.; Perepichka, D. F. J. Am. Chem. Soc. 2013, 135, 16585-16594. (b) Kastler, M.; Schmidt, J.; Pisula, W.; Sebastiani, D.; Müllen, K. J. Am. Chem. Soc. 2006, 128, 9526-9534. (c) Wu, J.; Pisula, W.; Müllen, K. Chem. Rev. 2007, 107, 718-747. (d) Debije, M. G.; Phis, J.; de Haas, M. P.; Warman, J. M.; Tomović, Z.; Simpson, C. D.; Watson, M. D.; Müllen, K. J. Am. Chem. Soc. 2004, 126, 4641-4645.

(8) (a) Pho, T.; Yuen, J. D.; Kurzman, J. A.; Smith, B. G.; Miao, M. S.; Walker, W. T.; Seshadri, R.; Wudl, F. J. Am. Chem. Soc. 2012, 134, 18185-18188. (b) Alonso, J. M.; Díaz-Álvarez, A. D.; Criado, A.; Pérez, D.; Peña, D.; Guitián, E. Angew. Chem. Int. Ed. 2012, 51, 173-177. (c) Okamoto, T.; Mitsui, C.; Yamagishi, M.; Nakahara, K.; Soeda, J.; Hirose, Y.; Miwa, K.; Sato, H.; Yamano, A.; Matsushita, T.; Uemura, T.; Takeya, J. Adv. Mater. 2013, 25, 6392-6397.

(9) (a) Zhang, L.; Fonari, A.; Zhang, Y.; Zhao, G.; Coropceanu, V.; Hu, W.; Parkin, S.; Brédas, J. L.; Briseno, A. L. Chem. Eur. J. 2013, 19, 17907-17916. (b) Zhang, L.; Walker, B.; Liu, F.; Colella, N. S.; Mannsfeld, S. C. B.; Watkins, J. J.; Nguyen, T.-Q.; Briseno, A. L. J. Mater. Chem. 2012, 22, 4266-4268.

(10) Clar, E. J. Chem. Soc. 1949, 2013-2016.

(11) Malkin, J. Photophysical and Photochemical Properties of Aromatic Compounds; CRC Press: Boca Raton, Fla., 1992.

(12) Stein, T.; Eisenberg, H.; Kronik, L.; Baer, R. Phys. Rev. Lett. 2010, 105, 266802-266804.

(13) Kaur, I.; Jia, W.; Kopreski, R. P.; Selvarasah, S.; Dokmeci, M. R.; Pramanik, C.; McGruer, N. E.; Miller, G. P. J. Am. Chem. Soc. 2008, 130, 16274-16286.

(14) Maliakal, A.; Raghavachari, K.; Katz, H.; Chandross, E.; Siegrist, T. Chem. Mater. 2004, 16, 4980-4986.

(15) (a) Anthony, J. E.; Eaton, D. L.; Parkin, S. R. Org. Lett. 2001, 4, 15-18. (b) Anthony, J. E.; Subramanian, S.; Parkin, S. R.; Park, S. K.; Jackson, T. N. J. Mater. Chem. 2009, 19, 7984-7989.

(16) Inokuchi, H.; Saito, G.; Wu, P.; Seki, K.; Tang, T. B.; Mori, T.; Imaeda, k.; Enoki, T.; Higuchi, Y.; Inaka, K.; Yasuoka, N. Chem. Lett. 1986, 15, 1263-1266.

(17) Coropceanu, V.; Li, H.; Winget, P.; Zhu, L.; Brédas, J. L. Annu. Rev. Mater. Res. 2013, 43, 63-87.

(18) (a) Salman, S.; Ruiz Delgado, M.; Coropceanu, V.; Brédas, J. L. Chem. Mater. 2009, 21, 3593-3601. (b) Liuolia, V.; Valkunas, L.; Grondelle, R. J. Phys. Chem. B 1997, 101, 7343-7349.

(19) Banville, J.; Beaulieu, F.; Martel, A.; Ouellet, C.; Ruediger, E.; Belema, M.; Qiu, Y.; Vysa, D.; Yang, X.; Zusi, F. C.; Burke, J.; Gregor, K.; MacMaster, J.; McIntyre, K.; Pattoli, A. Bioorganic and Medicinal Chemistry Letters, 2007, 17, 1233.

20) Dovesi, R.; Orlando, R.; Civalleri, B.; Roetti, C.; Saunders, V. R.; Zicovich-Wilson, C. M. Z. Kristallogr. 2005, 220, 571.

21) Valeev, E. F.; Coropceanu, V.; da Silva Filho, D. A.; Salman, S.; Brédas, J.-L. JACS 2006, 128, 9882.

(22) Valiev, M.; Bylaska, E. J.; Govind, N.; Kowalski, K.; Straatsma, T. P.; Van Dam, H. J. J.; Wang, D.; Nieplocha, J.; Apra, E.; Windus, T. L.; de Jong, W. A. Comput. Phys. Commun. 2010, 181, 1477.

(23) Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas; Foresman, J. B.; Ortiz, J. V.; Cioslowski, J.; Fox, D. J. Wallingford Conn., 2009.

24) Stein, T.; Eisenberg, H.; Kronik, L.; Baer, R. Phys. Rev. Lett. 2010, 105, 266802.

(25) Chai, J.-D.; Head-Gordon, M. J. Chem. Phys. 2008, 128.

What is claimed is:

1. A compound according to following structural formula:

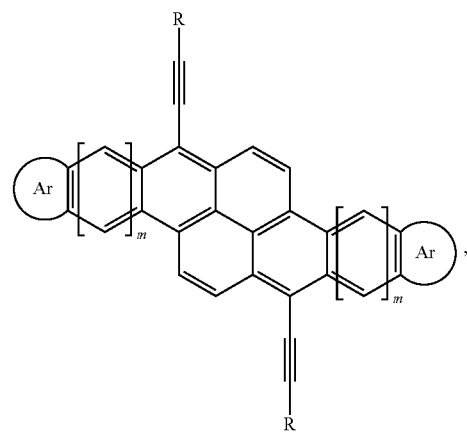

wherein:
Ar is benzene;
R is trimethylsilyl, triethylsilyl, triisopropylsilyl, or N-octyldiisopropylsilyl; and
m is an integer from 1 to 5.

2. The compound of claim 1, wherein R is trimethylsilyl or triethylsilyl.

3. A method of making a compound, the method comprising:
a) contacting

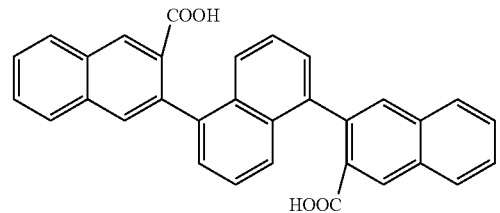 [SMILES: O=C(O)c1cc2ccccc2cc1-c1cccc2c(-c3cc4ccccc4cc3C(=O)O)cccc12]

with polyphosphoric acid to produce

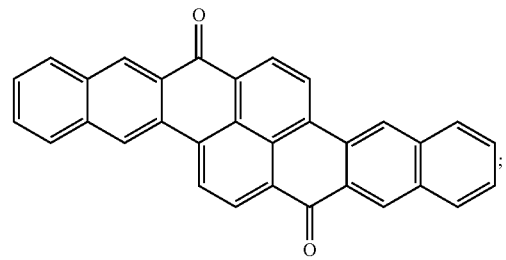 [SMILES: O=C1c2cc3ccccc3cc2-c2ccc3c4c(ccc1c24)-c1cc2ccccc2cc1C3=O]

b) contacting

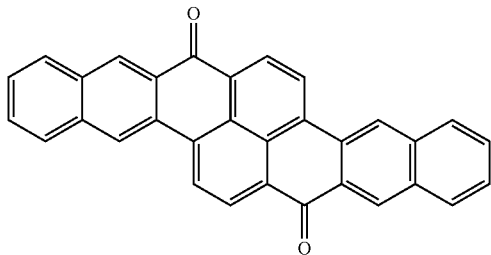 [SMILES: O=C1c2cc3ccccc3cc2-c2ccc3c4c(ccc1c24)-c1cc2ccccc2cc1C3=O]

with R-acetylene, THF, and n-butyl lithium, wherein R is triisopropylsilyl or N-octyldiisopropylsilyl;

c) contacting the result of b) with SnCl$_2$ in HCl, to thereby yield a compound having the formula:

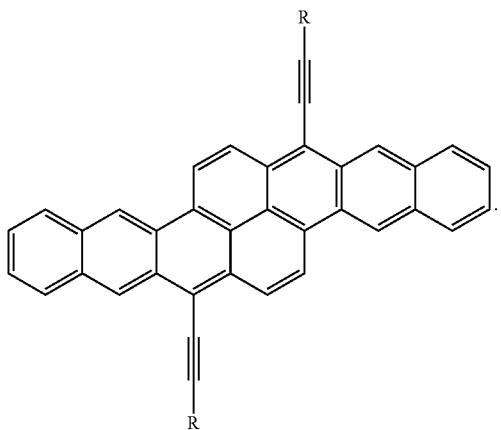

4. The method of claim 3, further comprising contacting

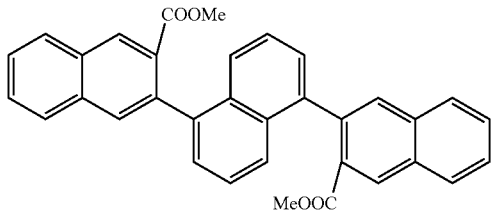 [SMILES: COC(=O)c1cc2ccccc2cc1-c1cccc2c(-c3cc4ccccc4cc3C(=O)OC)cccc12]

with KOH in MeOH and THF to yield

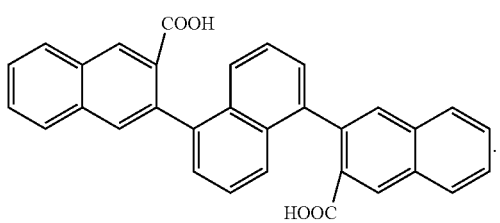 [SMILES: O=C(O)c1cc2ccccc2cc1-c1cccc2c(-c3cc4ccccc4cc3C(=O)O)cccc12]

5. The method of claim 4, further comprising contacting

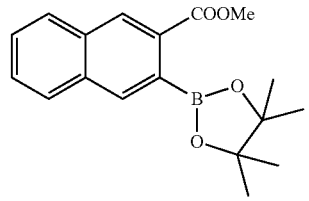 [SMILES: COC(=O)c1cc2ccccc2cc1B1OC(C)(C)C(C)(C)O1]

with 1,5-dibromonaphthalene, Pd(0), THF, and potassium carbonate to yield

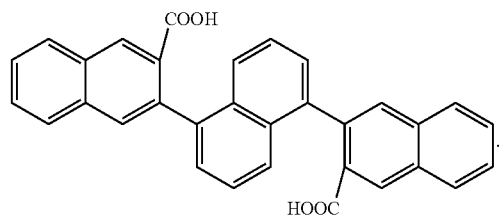 [SMILES: O=C(O)c1cc2ccccc2cc1-c1cccc2c(-c3cc4ccccc4cc3C(=O)O)cccc12]

6. The method of claim 5, wherein the Pd(0) is tetrakis(triphenylphosphine)-palladium(0).

7. A method of making a compound, the method comprising:

a) contacting

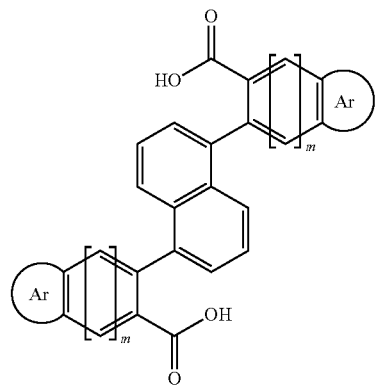

with polyphosphoric acid to produce

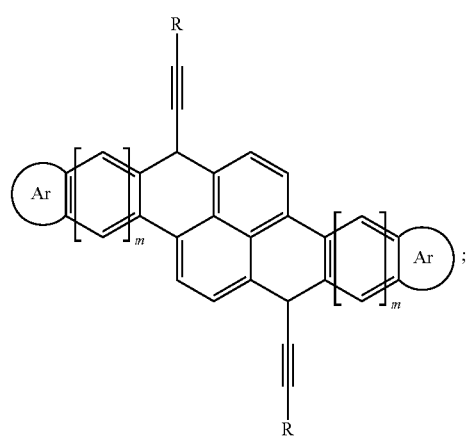

b) contacting

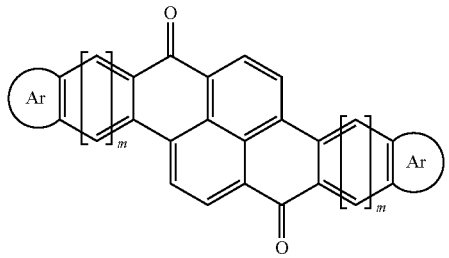

with R-acetylene, and n-butyl lithium;

c) contacting the result of b) with SnCl$_2$ in HCl, to thereby yield a compound having the formula:

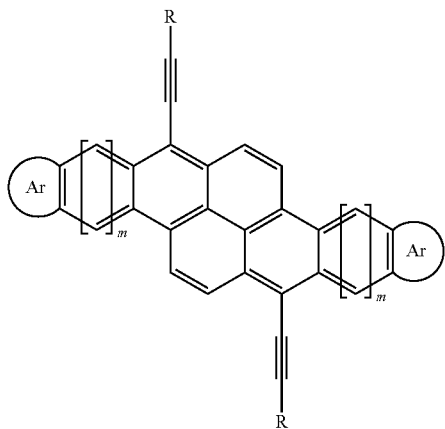

wherein:

Ar is benzene;

R is trimethylsilyl, triethylsilyl, triisopropylsilyl, or N-octyldiisopropylsilyl; and m is an integer from 1 to 5.

8. The method of claim 7, further comprising contacting

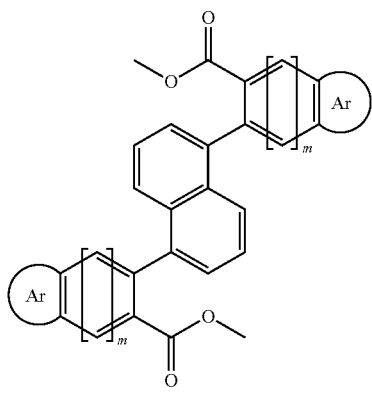

with KOH in MeOH and THF to yield

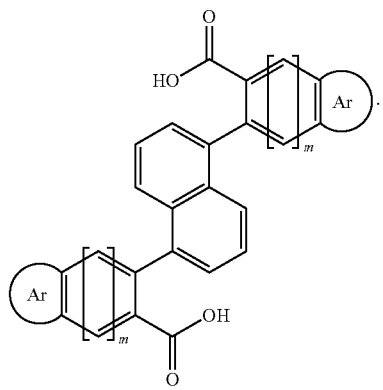

9. The method of claim 8, further comprising contacting

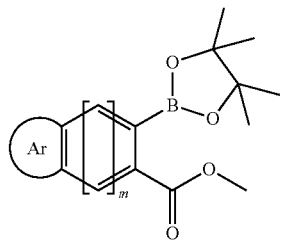

with 1, 5-dibromonaphthalene, Pd(0), THF, and potassium carbonate to yield

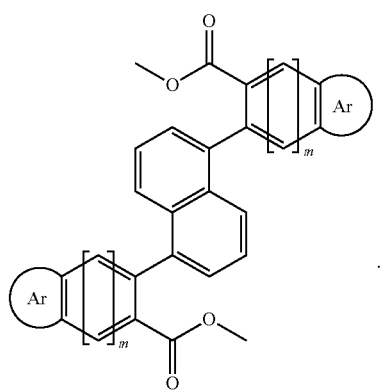

10. The method of claim 9, wherein the Pd(0) is tetrakis(triphenylphosphine)-palladium(0).

11. The compound of claim 1, wherein the compound has the following formula:

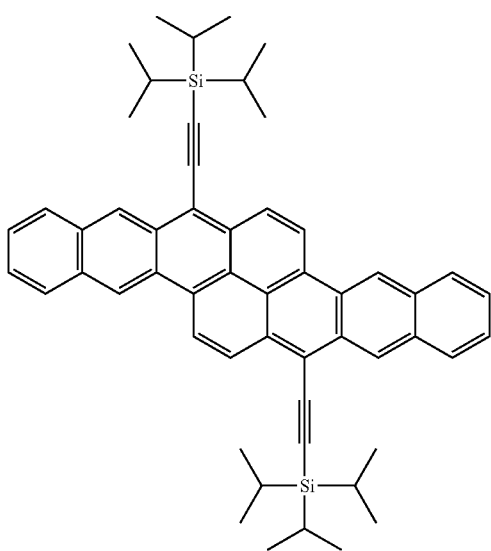

12. The compound of claim 1, wherein the compound has the following formula:

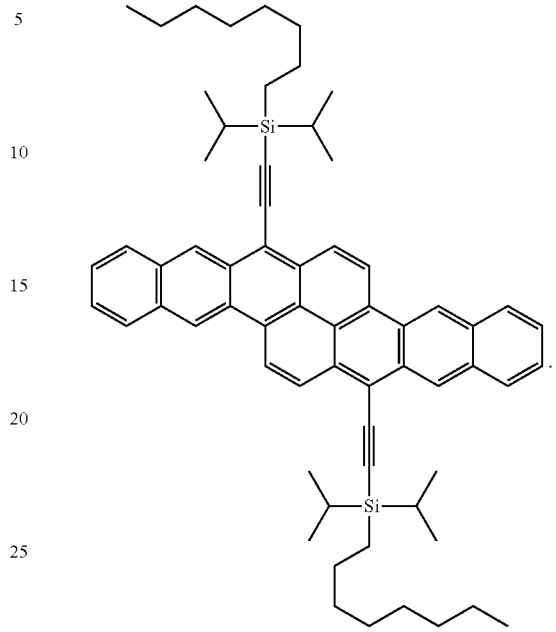

13. The method of claim 3, wherein R is triisopropylsilyl.
14. The method of claim 3, wherein R is N-octyldiisopropylsilyl.
15. The method of claim 7, wherein R is triisopropylsilyl.
16. The method of claim 7, wherein R is N-octyldiisopropylsilyl.

* * * * *

UNITED STATES PATENT AND TRADEMARK OFFICE
CERTIFICATE OF CORRECTION

PATENT NO. : 10,005,796 B2
APPLICATION NO. : 15/307968
DATED : June 26, 2018
INVENTOR(S) : Alejandro Briseno and Lei Zhang Page 1 of 1

It is certified that error appears in the above-identified patent and that said Letters Patent is hereby corrected as shown below:

In the Claims

In Claim 7, Column 22, Lines 50-70, please remove the structural formula, and insert the following structural formula:

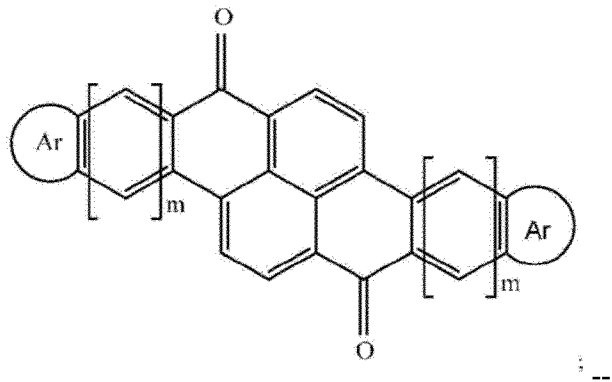

-- ; --

Signed and Sealed this
Twenty-eighth Day of August, 2018

Andrei Iancu
*Director of the United States Patent and Trademark Office*